(12) United States Patent
Shoham et al.

(10) Patent No.: US 9,782,363 B2
(45) Date of Patent: Oct. 10, 2017

(54) ANTI-VIRULANCE COMPOSITIONS AND METHODS

(71) Applicant: Case Western Reserve University, Cleveland, OH (US)

(72) Inventors: Menachem Shoham, Cleveland, OH (US); Rajesh Viswanathan, Cleveland, OH (US); Guanping Yu, Cleveland, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 14/435,387

(22) PCT Filed: Oct. 14, 2013

(86) PCT No.: PCT/US2013/064800
§ 371 (c)(1),
(2) Date: Apr. 13, 2015

(87) PCT Pub. No.: WO2014/059404
PCT Pub. Date: Apr. 17, 2014

(65) Prior Publication Data
US 2015/0265550 A1    Sep. 24, 2015

Related U.S. Application Data

(60) Provisional application No. 61/713,306, filed on Oct. 12, 2012.

(51) Int. Cl.
*A61K 31/12* (2006.01)
*A61K 31/192* (2006.01)
*A61K 31/235* (2006.01)
*C12N 1/20* (2006.01)
*A61K 45/06* (2006.01)
*A61K 9/00* (2006.01)
*A61K 31/122* (2006.01)

(52) U.S. Cl.
CPC ............ *A61K 31/12* (2013.01); *A61K 9/0014* (2013.01); *A61K 31/122* (2013.01); *A61K 31/192* (2013.01); *A61K 31/235* (2013.01); *A61K 45/06* (2013.01); *C12N 1/20* (2013.01)

(58) Field of Classification Search
CPC .... A61K 31/12; A61K 9/0014; A61K 31/192; A61K 31/235; A61K 45/06; A61K 31/122; A61K 2300/00; C12N 1/20
See application file for complete search history.

(56) References Cited

U.S. PATENT DOCUMENTS

| 2007/0148185 A1* | 6/2007 | Rathore | ............... C07K 14/445 424/191.1 |
| 2011/0218226 A1* | 9/2011 | Shoham | ................. A61K 31/12 514/411 |
| 2012/0142682 A1 | 6/2012 | Merrill | |

* cited by examiner

*Primary Examiner* — Sarah Pihonak
*Assistant Examiner* — Jason A Deck
(74) *Attorney, Agent, or Firm* — Tarolli, Sundheim, Covell & Tummino LLP

(57) ABSTRACT

A method of reducing the virulence of a bacterium that expresses accessory gene regulator A (AgrA) or an ortholog of AgrA includes administering to the bacterium an amount of a pharmaceutical composition effective to inhibit the synthesis of one or more virulence factors by the bacterium, the pharmaceutical composition including an AgrA antagonist.

7 Claims, 5 Drawing Sheets

A
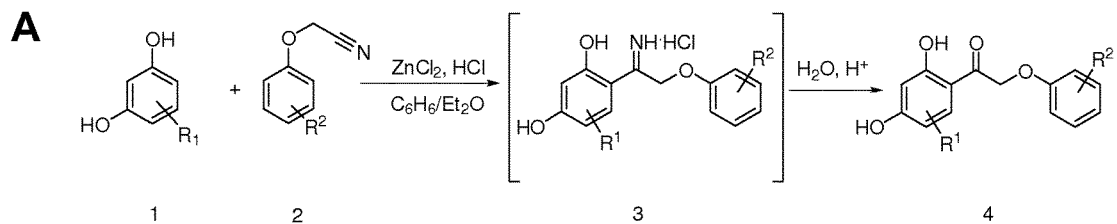
$R^1$ = H, 5-Et, 6-OH, 5-Me, 5-Pr, 5-hexyl
$R^2$ = F, Cl, Br, I, $NO_2$, Me, i-Pr, Ph, COOH, t-Bu, $OCH_3$, $COOCH_3$
B
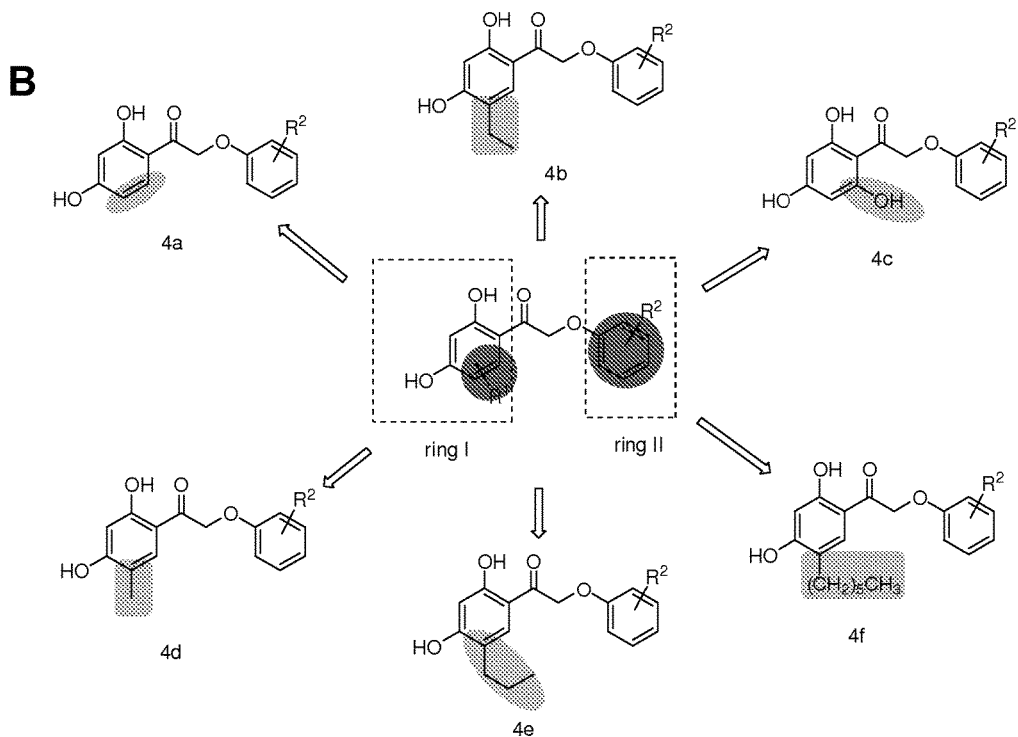
$R^2$ = F, Cl, Br, I, $NO_2$, Me, i-Pr, Ph, COOH, t-Bu, $OCH_3$, $COOCH_3$
Figs. 2A-B

ANTI-VIRULANCE COMPOSITIONS AND METHODS

RELATED APPLICATION

This application claims priority from U.S. Provisional Application No. 61/713,306, filed Oct. 12, 2012, the subject matter of which is incorporated herein by reference in its entirety.

TECHNICAL FIELD

This application relates to anti-virulence compositions and methods for treating bacterial infections and more particularly to compositions and methods for reducing the virulence of bacterium that expresses accessory gene regulator A (AgrA) or an ortholog of AgrA.

BACKGROUND

Resistance to existing antibiotics coupled with the decline in the development of new alternatives necessitates the search for agents to prevent and treat serious bacterial infections. Methicillin-Resistant *Staphylococcus Aureus* (MRSA) is the most widespread bacterial pathogen in the United States1 and in the developed world. MRSA causes a wide range of infections ranging from skin and soft tissue to more invasive forms, such as pneumonia, endocarditis, meningitis, bacteremia and sepsis. The increase in *S. aureus* infections has been associated with hospitalization, affecting preferentially immune compromised individuals. Recently, such infections also increasingly occur in the community in healthy individuals, such as athletes, students, prisoners, etc. These community-associated infections (CA-MRSA) are generally more virulent than hospital associated infections (HA-MRSA). Treatment of *S. aureus* infections is hampered by the steady increase of resistance against conventional antibiotics. Over two thirds of *S. aureus* infections are resistant to methicillin, a second-generation β-lactam antibiotic. Vancomycin, linezolid and daptomycin are the antibiotics of last resort against MRSA. Alarmingly, strains recently have emerged that are resistant to vancomycin. Therefore, the development of new therapeutic solutions against MRSA represents an urgent medical need.

Antivirulence agents present alternatives to conventional antibiotics. In contrast to antibiotics, antivirulence agents are not bactericidal, and generally are not even bacteriostatic. Their mechanism of action is based upon curtailing the pathogen's ability to elicit toxins against the host's immune system. An unimpaired immune system may be able to fight off the infection on its own. Alternatively, a boost in the form of a low-dose conventional antibiotic in combination with an antivirulence agent may become a successful strategy against more invasive infections. Antivirulence therapy offers the attractive prospect of bringing back conventional and affordable antibiotics into the clinic.

SUMMARY

Embodiments described herein relate to anti-virulence compositions and methods for treating bacterial infections and more particularly to compositions and methods for reducing the virulence of bacteria that express accessory gene regulator A (AgrA) or an ortholog of AgrA. The anti-virulence compositions described herein can act gene regulator A (AgrA) antagonists to inhibit activation of AgrA in the bacteria and inhibit virulence of the bacteria.

In some embodiment, the AgrA antagonist includes the following general formula:

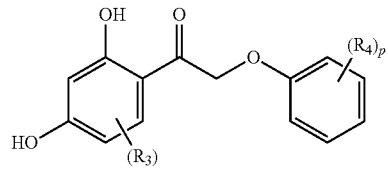

wherein $R_3$ and $R_4$ are each independently hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl containing from 5-6 ring atoms (wherein from 1-3 of the ring atoms is independently selected from N, NH, N($C_1$-$C_6$ alkyl), NC(O)($C_1$-$C_6$ alkyl), O, and S), $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—NH$_2$), carbamido (—NH—(CO)—NH$_2$), cyano (—CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—NH$_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O$^-$)$_2$), phosphinato (—P(O)(O$^-$)), phospho (—PO$_2$), phosphino (—PH$_2$), and combinations thereof; p is an integer from 0-5; and pharmaceutically acceptable salts thereof.

In other embodiments, $R_3$ is selected from the group consisting of H, halo, hydroxyl, substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, and heterocycloalkenyl; $R_4$ is selected from the group consisting of H, halo, nitro, hydroxyl, substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl, $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), and carboxylato (—COO$^-$); p is an integer from 0-5, and pharmaceutically acceptable salts thereof.

In yet other embodiments, $R_3$ is selected from the group consisting of H, substituted or unsubstituted 5-$C_1$-$C_6$ alkyl, and 6-OH; $R_4$ is selected from the group consisting of halo, nitro, substituted or unsubstituted $C_1$-$C_6$ alkyl, $C_3$-$C_{20}$ aryl, COOH, OCH$_3$, and COOCH$_3$; wherein p is an integer from 0-5; and pharmaceutically acceptable salts thereof.

In still other embodiments, $R_3$ is selected from the group consisting of H, 5-Et, 6-OH, 5-Me, 5-Pr, and 5-Hexyl; $R_4$ is selected from the group consisting of F, Cl, Br, I, NO$_2$, Me, i-Pr, Ph, COOH, t-Bu, OCH$_3$, and COOCH$_3$; wherein p is an integer from 0-5; and pharmaceutically acceptable salts thereof.

In some embodiments, the AgrA antagonist can be provided in a pharmaceutical composition with a pharmaceutically acceptable carrier. The composition can be, for example, a topical composition.

Other embodiments described herein relate to a method of treating a bacterial infection in a subject. The method includes administering to the subject an amount of an AgrA antagonist effective to inhibit the synthesis of one or more virulence factors by the bacteria. The AgrA antagonist can include the following general formula:

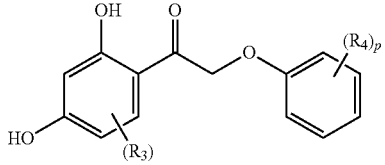

wherein $R_3$ and $R_4$ are each independently hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl containing from 5-6 ring atoms (wherein from 1-3 of the ring atoms is independently selected from N, NH, N($C_1$-$C_6$ alkyl), NC(O)($C_1$-$C_6$ alkyl), O, and S), $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—NH$_2$), carbamido (—NH—(CO)—NH$_2$), cyano (—CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—NH$_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O$^-$)$_2$), phosphinato (—P(O)(O$^-$)), phospho (—PO$_2$), phosphino (—PH$_2$), and combinations thereof; p is an integer from 0-5; and pharmaceutically acceptable salts thereof.

A further aspect of the application relates to a method of treating a bacterial infection related disease or disorder in a subject. The method includes administering to the subject an amount of an AgrA antagonist effective to inhibit the synthesis of one or more virulence factors by a bacterium in the subject. The pharmaceutical composition includes an AgrA antagonist having the general formula: The AgrA antagonist can include the following general formula:

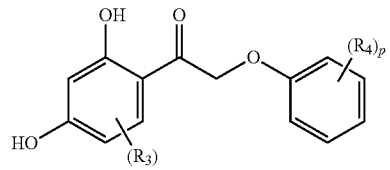

wherein $R_3$ and $R_4$ are each independently hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl containing from 5-6 ring atoms (wherein from 1-3 of the ring atoms is independently selected from N, NH, N($C_1$-$C_6$ alkyl), NC(O)($C_1$-$C_6$ alkyl), O, and S), $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—NH$_2$), carbamido (—NH—(CO)—NH$_2$), cyano (—CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—NH$_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)$^-$alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O$^-$)$_2$), phosphinato (—P(O)(O$^-$)), phospho (—PO$_2$), phosphino (—PH$_2$), and combinations thereof; p is an integer from 0-5; and pharmaceutically acceptable salts thereof.

BRIEF DESCRIPTION OF THE DRAWINGS

FIGS. 2(A-B) illustrates a (A) a reaction scheme and (B) compounds formed using the reaction scheme.

DETAILED DESCRIPTION

Figure 1:
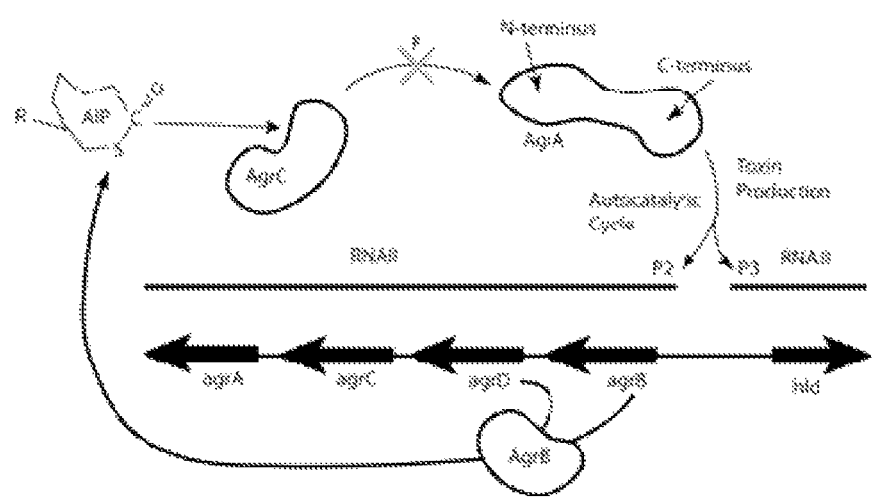
FIG. 1 is a schematic drawing of *S. aureus* agr operon for toxin production.

Methods involving conventional molecular biology techniques are described herein. Such techniques are generally known in the art and are described in detail in methodology treatises, such as *Current Protocols in Molecular Biology*, ed. Ausubel et al., Greene Publishing and Wiley-Interscience, New York, 1992 (with periodic updates). Unless otherwise defined, all technical terms used herein have the same meaning as commonly understood by one of ordinary skill in the art to which the present invention pertains. Commonly understood definitions of molecular biology terms can be found in, for example, Lodish et al., *Molecular Cell Biology*, 6th Edition, W. H. Freeman: New York, 2007, and Lewin, *Genes IX*, Jones and Bartlett Publishers: Mass., 2008. The definitions provided herein are to facilitate understanding of certain terms used frequently herein and are not meant to limit the scope of the application.

The articles "a" and "an" are used herein to refer to one or to more than one (i.e., to at least one) of the grammatical object of the article. By way of example, "an element" means one element or more than one element.

The terms "comprise," "comprising," "include," "including," "have," and "having" are used in the inclusive, open sense, meaning that additional elements may be included. The terms "such as", "e.g.", as used herein are non-limiting and are for illustrative purposes only. "Including" and "including but not limited to" are used interchangeably.

The term "or" as used herein should be understood to mean "and/or", unless the context clearly indicates otherwise.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length ±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

The terms "reducing", "suppressing" and "inhibiting" have their commonly understood meaning of lessening or decreasing.

The terms "effective," "effective amount," and "therapeutically effective amount" refer to that amount of an AgrA antagonist and/or a pharmaceutical composition thereof that inhibits the synthesis of one or more virulence factors by a bacterium or that results in amelioration of symptoms or a prolongation of survival in a subject with a bacteria related disease or disorder.

The phrases "parenteral administration" and "administered parenterally" are art-recognized terms, and include modes of administration other than enteral and topical administration, such as injections, and include, without limitation, intravenous, intramuscular, intrapleural, intravascular, intrapericardial, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrastemal injection and infusion.

The term "treatment" or "treating" refers to any therapeutic intervention in a mammal, including: (i) prevention, that is, causing the clinical symptoms not to develop, e.g., preventing infection from occurring and/or developing to a harmful state; (ii) inhibition, that is, arresting the development of clinical symptoms, e.g., stopping an ongoing infection so that the infection is eliminated completely or to the degree that it is no longer harmful; and/or (iii) relief, that is, causing the regression of clinical symptoms, e.g., causing a relief of fever and/or inflammation caused by an infection.

The term "preventing" is art-recognized and includes stopping a disease, disorder or condition from occurring in a subject, which may be predisposed to the disease, disorder and/or condition but has not yet been diagnosed as having it. Preventing a condition related to a disease includes stopping the condition from occurring after the disease has been diagnosed but before the condition has been diagnosed.

The term "pharmaceutical composition" refers to a formulation containing the disclosed compounds in a form suitable for administration to a subject. In a preferred embodiment, the pharmaceutical composition is in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of the disclosed compound or salts thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, intranasal, inhalational, and the like. Dosage forms for the topical or transdermal administration of a compound described herein includes powders, sprays, ointments, pastes, creams, lotions, gels, solutions, patches, nebulized compounds, and inhalants. In a preferred embodiment, the active compound is mixed under sterile conditions with a pharmaceutically acceptable carrier, and with any preservatives, buffers, or propellants that are required.

The terms "pharmaceutically acceptable" or "therapeutically acceptable" refers to a substance which does not interfere with the effectiveness or the biological activity of the active ingredients and which is not toxic to the host.

The phrase "pharmaceutically acceptable carrier" is art-recognized, and includes, for example, pharmaceutically acceptable materials, compositions or vehicles, such as a liquid or solid filler, diluent, excipient, solvent or encapsulating material, involved in carrying or transporting any subject composition from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The compounds of the application are capable of further forming salts. All of these forms are also contemplated herein.

"Pharmaceutically acceptable salt" of a compound means a salt that is pharmaceutically acceptable and that possesses the desired pharmacological activity of the parent compound. For example, the salt can be an acid addition salt. One embodiment of an acid addition salt is a hydrochloride salt. The pharmaceutically acceptable salts can be synthesized from a parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile being preferred. Lists of salts are found in Remington's Pharmaceutical Sciences, 18th ed. (Mack Publishing Company, 1990).

The compounds described herein can also be prepared as esters, for example pharmaceutically acceptable esters. For example, a carboxylic acid function group in a compound can be converted to its corresponding ester, e.g., a methyl, ethyl, or other ester. Also, an alcohol group in a compound can be converted to its corresponding ester, e.g., an acetate, propionate, or other ester.

The compounds described herein can also be prepared as prodrugs, for example pharmaceutically acceptable prodrugs. The terms "pro-drug" and "prodrug" are used interchangeably herein and refer to any compound, which releases an active parent drug in vivo. Since prodrugs are known to enhance numerous desirable qualities of pharmaceuticals (e.g., solubility, bioavailability, manufacturing, etc.) the compounds can be delivered in prodrug form. Thus, the compounds described herein are intended to cover prodrugs of the presently claimed compounds, methods of delivering the same and compositions containing the same. "Prodrugs" are intended to include any covalently bonded carriers that release an active parent drug in vivo when such prodrug is administered to a subject. Prodrugs are prepared by modifying functional groups present in the compound in such a way that the modifications are cleaved, either in routine manipulation or in vivo, to the parent compound. Prodrugs include compounds wherein a hydroxy, amino, sulfhydryl, carboxy, or carbonyl group is bonded to any group that may be cleaved in vivo to form a free hydroxyl, free amino, free sulfhydryl, free carboxy or free carbonyl group, respectively.

Examples of prodrugs include, but are not limited to, esters (e.g., acetate, dialkylaminoacetates, formates, phosphates, sulfates, and benzoate derivatives) and carbamates (e.g., N,N-dimethylaminocarbonyl) of hydroxy functional groups, ester groups (e.g., ethyl esters, morpholinoethanol esters) of carboxyl functional groups, N-acyl derivatives (e.g., N-acetyl)N-Mannich bases, Schiff bases and enaminones of amino functional groups, oximes, acetals, ketals and enol esters of ketone and aldehyde functional groups in compounds of Formula I, and the like, See Bundegaard, H. "Design of Prodrugs" p 1-92, Elesevier, New York-Oxford (1985).

The term "protecting group" refers to a grouping of atoms that when attached to a reactive group in a molecule masks, reduces or prevents that reactivity. Examples of protecting groups can be found in Green and Wuts, Protective Groups in Organic Chemistry, (Wiley, 2.sup.nd ed. 1991); Harrison and Harrison et al., Compendium of Synthetic Organic Methods, Vols. 1-8 (John Wiley and Sons, 1971-1996); and Kocienski, Protecting Groups, (Verlag, $3^{rd}$ ed. 2003).

A "patient," "subject," or "host" to be treated by the subject method may mean either a human or non-human animal, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder.

The term "in vitro" refers to an artificial environment and to processes or reactions that occur within an artificial environment. In vitro environments include, but are not limited to, test tubes and cell culture. The term "in vivo" refers to the natural environment (e.g., an animal or a cell) and to processes or reaction that occur within a natural environment. The term "in silico" refers to a process that is performed on a computer or is simulated on a computer or in virtual reality.

The term "AgrA antagonist" refers to any molecule with the capability of substantially reducing or inhibiting the activity of AgrA, for example, by blocking with at least some degree of effectiveness, the phospho-histidine pocket of AgrA. This invention focuses most strongly on small molecules as AgrA antagonists described and further identified by the methods set forth herein.

The term "small molecule" can refer to lipids, carbohydrates, polynucleotides, polypeptides, or any other organic or inorganic molecules.

The phrase "having the formula" or "having the structure" is not intended to be limiting and is used in the same way that the term "comprising" is commonly used.

The term "analog" can mean a compound in which one or more individual atoms have been replaced, either with a different atom or with a different functional group, and where replacement of the atom does not substantially eliminate or reduce the compound's ability to act as an AgrA antagonist.

The term "ortholog" denotes the well-known meaning of this term. In this art, orthologs are genes in different species which evolved from a common ancestral gene. Due to their separation following a speciation event, orthologs may diverge, but usually have similarity at the sequence and structure levels; furthermore, orthologs usually have identical functions. Orthology is a type of homology. In this application, the term ortholog is used to include the ortholog gene (DNA or RNA) or the peptide/protein product of the ortholog. Sometimes the peptide/protein product of the ortholog is referred to as "ortholog product" or simply "ortholog". The meaning is evident from the context (e.g., an anti-virulence compositions of the present invention may include an anti-virulence agent capable of reducing the virulence of bacterium that expresses peptides or proteins that may be referred to as orthologs of AgrA-that is, products of an ortholog gene of *Staphylococcus aureus* AgrA from another bacterium, such as *Streptococcus pyogenes*). In certain aspects, an ortholog of AgrA produces proteins/ peptides that share greater than about 70%, about 80%, or about 90% identity with the amino acid sequence of the gene product of AgrA.

The terms "prophylactic" or "therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic (i.e., it is intended to diminish, ameliorate, or stabilize the existing unwanted condition or side effects thereof).

The terms "therapeutic agent", "drug", "medicament" and "bioactive substance" are art-recognized and include molecules and other agents that are biologically, physiologically, or pharmacologically active substances that act locally or systemically in a patient or subject to treat a disease or condition. The terms include without limitation pharmaceutically acceptable salts thereof and prodrugs. Such agents may be acidic, basic, or salts; they may be neutral molecules, polar molecules, or molecular complexes capable of hydrogen bonding; they may be prodrugs in the form of ethers, esters, amides and the like that are biologically activated when administered into a patient or subject.

The phrase "therapeutically effective amount" or "pharmaceutically effective amount" is an art-recognized term. In certain embodiments, the term refers to an amount of a therapeutic agent that produces some desired effect at a reasonable benefit/risk ratio applicable to any medical treatment. In certain embodiments, the term refers to that amount necessary or sufficient to eliminate, reduce or maintain a target of a particular therapeutic regimen. The effective amount may vary depending on such factors as the disease or condition being treated, the particular targeted constructs being administered, the size of the subject or the severity of the disease or condition. One of ordinary skill in the art may empirically determine the effective amount of a particular compound without necessitating undue experimentation. In certain embodiments, a therapeutically effective amount of a therapeutic agent for in vivo use will likely depend on a number of factors, including: the rate of release of an agent from a polymer matrix, which will depend in part on the chemical and physical characteristics of the polymer; the identity of the agent; the mode and method of administration; and any other materials incorporated in the polymer matrix in addition to the agent.

The term "ED50" is art-recognized. In certain embodiments, ED50 means the dose of a drug, which produces 50% of its maximum response or effect, or alternatively, the dose, which produces a pre-determined response in 50% of test subjects or preparations. The term "LD50" is art-recognized. In certain embodiments, LD50 means the dose of a drug, which is lethal in 50% of test subjects. The term "therapeutic index" is an art-recognized term, which refers to the therapeutic index of a drug, defined as LD50/ED50.

The terms "$IC_{50}$," or "half maximal inhibitory concentration" is intended to refer to the concentration of a substance (e.g., a compound or a drug) that is required for 50% inhibition of a biological process, or component of a process, including a protein, subunit, organelle, ribonucleoprotein, etc.

With respect to any chemical compounds, the present application is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

When a bond to a substituent is shown to cross a bond connecting two atoms in a ring, then such substituent can be bonded to any atom in the ring. When a substituent is listed without indicating the atom via which such substituent is bonded to the rest of the compound of a given formula, then such substituent can be bonded via any atom in such substituent. Combinations of substituents and/or variables are permissible, but only if such combinations result in stable compounds.

When an atom or a chemical moiety is followed by a subscripted numeric range (e.g., $C_{1-6}$), it is meant to encompass each number within the range as well as all intermediate ranges. For example, "$C_{1-6}$ alkyl" is meant to include alkyl groups with 1, 2, 3, 4, 5, 6, 1-6, 1-5, 1-4, 1-3, 1-2, 2-6, 2-5, 2-4, 2-3, 3-6, 3-5, 3-4, 4-6, 4-5, and 5-6 carbons.

The term "alkyl" is intended to include both branched (e.g., isopropyl, tert-butyl, isobutyl), straight-chain e.g., methyl, ethyl, propyl, butyl, pentyl, hexyl, heptyl, octyl, nonyl, decyl), and cycloalkyl (e.g., alicyclic) groups (e.g., cyclopropyl, cyclopentyl, cyclohexyl, cycloheptyl, cyclooctyl), alkyl substituted cycloalkyl groups, and cycloalkyl substituted alkyl groups. Such aliphatic hydrocarbon groups have a specified number of carbon atoms. For example, $C_{1-6}$ alkyl is intended to include $C_1$, $C_2$, $C_3$, $C_4$, $C_5$, and $C_6$ alkyl groups. As used herein, "lower alkyl" refers to alkyl groups having from 1 to 6 carbon atoms in the backbone of the carbon chain. "Alkyl" further includes alkyl groups that have oxygen, nitrogen, sulfur or phosphorous atoms replacing one or more hydrocarbon backbone carbon atoms. In certain embodiments, a straight chain or branched chain alkyl has six or fewer carbon atoms in its backbone (e.g., $C_1$-$C_6$ for straight chain, $C_3$-$C_6$ for branched chain), for example four or fewer. Likewise, certain cycloalkyls have from three to eight carbon atoms in their ring structure, such as five or six carbons in the ring structure.

The term "substituted alkyls" refers to alkyl moieties having substituents replacing a hydrogen on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "aralkyl" moiety is an alkyl substituted with an aryl (e.g., phenylmethyl (benzyl)). If not otherwise indicated, the terms "alkyl"

and "lower alkyl" include linear, branched, cyclic, unsubstituted, substituted, and/or heteroatom-containing alkyl or lower alkyl, respectively.

The term "alkenyl" refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, cyclopentenyl, cyclohexenyl, cyclooctenyl, and the like. Generally, although again not necessarily, alkenyl groups can contain 2 to about 18 carbon atoms, and more particularly 2 to 12 carbon atoms. The term "lower alkenyl" refers to an alkenyl group of 2 to 6 carbon atoms, and the specific term "cycloalkenyl" intends a cyclic alkenyl group, preferably having 5 to 8 carbon atoms. The term "substituted alkenyl" refers to alkenyl substituted with one or more substituent groups, and the terms "heteroatom-containing alkenyl" and "heteroalkenyl" refer to alkenyl or heterocycloalkenyl (e.g., heterocylcohexenyl) in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" refers to a linear or branched hydrocarbon group of 2 to 24 carbon atoms containing at least one triple bond, such as ethynyl, n-propynyl, and the like. Generally, although again not necessarily, alkynyl groups can contain 2 to about 18 carbon atoms, and more particularly can contain 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The terms "alkyl", "alkenyl", and "alkynyl" are intended to include moieties which are diradicals, i.e., having two points of attachment. A nonlimiting example of such an alkyl moiety that is a diradical is —$CH_2CH_2$—, i.e., a $C_2$ alkyl group that is covalently bonded via each terminal carbon atom to the remainder of the molecule.

The term "alkoxy" refers to an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Preferred substituents identified as "$C_1$-$C_6$ alkoxy" or "lower alkoxy" herein contain 1 to 3 carbon atoms, and particularly preferred such substituents contain 1 or 2 carbon atoms (i.e., methoxy and ethoxy).

The term "aryl" refers to an aromatic substituent containing a single aromatic ring or multiple aromatic rings that are fused together, directly linked, or indirectly linked (such that the different aromatic rings are bound to a common group such as a methylene or ethylene moiety). Aryl groups can contain 5 to 20 carbon atoms, and particularly preferred aryl groups can contain 5 to 14 carbon atoms. Examples of aryl groups include benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkylamino, dialkylamino, arylamino, diaryl amino, and al kylaryl amino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, methylenedioxyphenyl). If not otherwise indicated, the term "aryl" includes unsubstituted, substituted, and/or heteroatom-containing aromatic substituents.

The term "alkaryl" refers to an aryl group with an alkyl substituent, and the term "aralkyl" refers to an alkyl group with an aryl substituent, wherein "aryl" and "alkyl" are as defined above. Exemplary aralkyl groups contain 6 to 24 carbon atoms, and particularly preferred aralkyl groups contain 6 to 16 carbon atoms. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. Alkaryl groups include, for example, p-methylphenyl, 2,4-dimethylphenyl, p-cyclohexylphenyl, 2,7-dimethylnaphthyl, 7-cyclooctylnaphthyl, 3-ethyl-cyclopenta-1,4-diene, and the like.

The terms "heterocyclyl" or "heterocyclic group" include closed ring structures, e.g., 3- to 10-, or 4- to 7-membered rings, which include one or more heteroatoms. "Heteroatom" includes atoms of any element other than carbon or hydrogen. Examples of heteroatoms include nitrogen, oxygen, sulfur and phosphorus.

Heterocyclyl groups can be saturated or unsaturated and include pyrrolidine, oxolane, thiolane, piperidine, piperazine, morpholine, lactones, lactams, such as azetidinones and pyrrolidinones, sultams, and sultones. Heterocyclic groups such as pyrrole and furan can have aromatic character. They include fused ring structures, such as quinoline and isoquinoline. Other examples of heterocyclic groups include pyridine and purine. The heterocyclic ring can be substituted at one or more positions with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety. Heterocyclic groups can also be substituted at one or more constituent atoms with, for example, a lower alkyl, a lower alkenyl, a lower alkoxy, a lower alkylthio, a lower alkylamino, a lower alkylcarboxyl, a nitro, a hydroxyl, —$CF_3$, or —CN, or the like.

The term "halo" or "halogen" refers to fluoro, chloro, bromo, and iodo. "Counterion" is used to represent a small, negatively charged species such as fluoride, chloride, bromide, iodide, hydroxide, acetate, and sulfate.

The terms "substituted" as in "substituted alkyl," "substituted aryl," and the like, as alluded to in some of the aforementioned definitions, is meant that in the alkyl, aryl, or other moiety, at least one hydrogen atom bound to a carbon (or other) atom is replaced with one or more non-hydrogen substituents. Examples of such substituents include, without limitation: functional groups such as halo, hydroxyl, silyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO—), carbamoyl (—(CO)—$NH_2$), mono-($C_1$-$C_{24}$ alkyl)-substituted carbamoyl (—(CO)—NH($C_1$-$C_{24}$ alkyl)), di-($C_1$-$C_4$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—$NH_2$), carbamido (—NH—(CO)—$NH_2$), cyano (—CN), isocyano (—$N^+C^-$), cyanato (—O—CN), isocyanato (—$ON^+C^-$), isothiocyanato (—S—CN), azido (—N=$N^+$=$N^-$), formyl (—(CO)—H), thioformyl (—(CS)—H), amino (—$NH_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino (—CR=NH where R=hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, etc.), arylimino (—CR=N (aryl), where R=hydrogen, alkyl, aryl, alkaryl, etc.), nitro (—$NO_2$), nitroso (—NO), sulfo (—$SO_2$—OH), sulfonato (—$SO_2$—$O^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—$SO_2$-alkyl), $C_5$-$C_{20}$ arylsulfonyl (—$SO_2$-aryl), phosphono (—P(O)(OH)$_2$), phosphonato (—P(O)($O^-$)$_2$), phosphinato (—P(O)($O^-$)), phospho (—$PO_2$), and phosphino (—$PH_2$); and the hydrocarbyl moieties $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, and $C_6$-$C_{24}$ aralkyl.

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. For example, the phrase "substituted alkyl, alkenyl, and aryl" is to be interpreted as "substituted alkyl, substituted alkenyl, and substituted aryl." Analogously, when the term "heteroatom-containing" appears prior to a list of possible heteroatom-containing groups, it is intended that the term apply to every member of that group. For example, the phrase "heteroatom-containing alkyl, alkenyl, and aryl" is to be interpreted as "heteroatom-containing alkyl, substituted alkenyl, and substituted aryl.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

The terms "stable compound" and "stable structure" are meant to indicate a compound that is sufficiently robust to survive isolation, and as appropriate, purification from a reaction mixture, and formulation into an efficacious therapeutic agent.

The terms "free compound" is used herein to describe a compound in the unbound state.

Throughout the description, where compositions are described as having, including, or comprising, specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the compositions and methods described herein remains operable. Moreover, two or more steps or actions can be conducted simultaneously.

The term "small molecule" is an art-recognized term. In certain embodiments, this term refers to a molecule, which has a molecular weight of less than about 2000 amu, or less than about 1000 amu, and even less than about 500 amu.

Embodiments described herein relate to anti-virulence compositions and methods for treating bacterial infections and more particularly to compositions and methods for reducing the virulence of bacterium that expresses accessory gene regulator A (AgrA) or an ortholog of AgrA.

The accessory gene regulator (agr) system represents an operon that controls the expression of virulence factors in Gram-positive bacteria (Kleerebezem M, Quadri L E, Kuipers O P and de Vos W M (1997) Quorum sensing by peptide pheromones and two-component signal-transduction systems in Gram-positive bacteria. Molecular Microbiology 24:895). The agr operon contains two sets of genes that code for two sets of mRNA called RNAII and RNAIII. The two parts of the operon are transcribed in opposite directions, each with its own promoter P2 and P3.

As shown in FIG. 1, the products of the agr system include the autoinducer peptide (AIP), encoded by AgrD and processed and exported by AgrB. The autoinducing peptide (AIP) has a thiolactone structure. AIP binds to and activates the histidine kinase AgrC, which in turn binds to the N-terminal domain of AgrA to phosphorylate an aspartate residue in the binding pocket. The C-terminal DNA-binding domain of AgrA acts as a transcription factor that activates both promoters P2 and P3. Consequently, phosphorylated AgrA promotes further production of AIP in the autocatalytic RNAII cycle via the P2 promoter and concomitantly activates P3 leading to the induction of RNAIII Being the effector of the agr system, RNAIII initiates the transcription of genes that encode a variety of virulence factors, e.g., hla (encoding α-hemolysin), psm-α (phenol-soluble modulin-α), saeB (enterotoxin B), tst (TSST-1), ssp and spr (serine proteases). Compounds and methods that can block phosphorylation and/or activation of AgrA in bacterium expressing AgrA (as illustrated by the X in FIG. 1) can reduce the virulence of the bacterium by inhibiting the production and excretion of one or more bacterium virulence factors and can further be used to treat or prevent bacterial infections and related diseases and disorders in a subject.

An aspect of the application therefore relates to a method of reducing the virulence of a bacterium that expresses AgrA by administering to the bacterium an amount of AgrA antagonist or pharmaceutical composition thereof effective to inhibit the synthesis of one or more virulence factors by the bacterium.

Bacteria in accordance with this application that can be treated with the AgrA antagonist can include those bacteria expressing AgrA associated with pathogenic association with another organism, bacterial infection, and widespread disease. In some embodiments, bacteria treated by the AgrA antagonist can include gram-positive bacteria, such as *Staphylococcus* and *Streptococcus*. In some embodiments, the bacteria can be antibiotic resistant methicillin-resistant *Staphylococcus aureus* (MRSA). In other embodiments, the bacteria can be *Streptococcus pyogenes*.

Virulence factors as contemplated herein include any molecules expressed and secreted by bacteria to promote colonization and/or adhesion in a host subject, promote evasion of the host's immune response and obtain nutrition from the host subject. Virulence factors can also include both exotoxins and endotoxins.

Non-limiting examples of virulence factors inhibited by an AgrA antagonist described herein include one or more of a protease (e.g., serine proteases), nuclease, lipase, coagulase, hyaluronidase, clumping factor, pyrogenic toxin superantigen (e.g., TSST-1), enterotoxins (e.g., enterotoxin B), exfoliative toxin, leukotoxin, along with α, β, γ, γ-variant, and δ-hemolysins. In some aspects, the virulence factor inhibited is α-hemolysin.

In certain embodiments, small molecule compounds that affect (e.g., reduces, inhibits, eliminates, or ameliorates) the activity of AgrA and that can be used as an AgrA antagonist as described herein can include a compounds having the general formula:

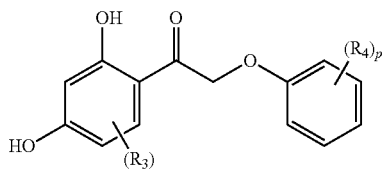

wherein $R_3$ and $R_4$ are each independently hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl containing from 5-6 ring atoms (wherein from 1-3 of the ring atoms is independently selected from N, NH, N($C_1$-$C_6$ alkyl), NC(O)($C_1$-$C_6$ alkyl), O, and S), $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—NH$_2$), carbamido (—NH—(CO)—NH$_2$), cyano (—CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—NH$_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O), $C_1$-$C_{24}$ alkyl-sulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O)$_2$), phosphinato (—P(O)(O$^-$)), phospho (—PO$_2$), phosphino (—PH$_2$), and combinations thereof; p is an integer from 0-5; and pharmaceutically acceptable salts thereof.

In other embodiments, $R_3$ is selected from the group consisting of H, halo, hydroxyl, substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, and heterocycloalkenyl; $R_4$ is selected from the group consisting of H, halo, nitro, hydroxyl, substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl, $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), and carboxylato (—COO$^-$); p is an integer from 0-5, and pharmaceutically acceptable salts thereof In yet other embodiments, $R_3$ is selected from the group consisting of H, substituted or unsubstituted 5-$C_1$-$C_6$ alkyl, and 6-OH; $R_4$ is selected from the group consisting of halo, nitro, substituted or unsubstituted $C_1$-$C_6$ alkyl, $C_3$-$C_{20}$ aryl, COOH, OCH$_3$, and COOCH$_3$; wherein p is an integer from 0-5; and pharmaceutically acceptable salts thereof.

In still other embodiments, $R_3$ is selected from the group consisting of H, 5-Et, 6-OH, 5-Me, 5-Pr, and 5-Hexyl; $R_4$ is selected from the group consisting of F, Cl, Br, I, NO$_2$, Me, i-Pr, Ph, COOH, t-Bu, OCH$_3$, and COOCH$_3$; wherein p is an integer from 0-5; and pharmaceutically acceptable salts thereof.

In some embodiments, the AgrA antagonist can include the general formula (4a):

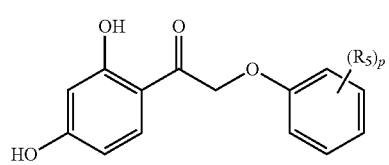

(4a)

wherein $R_5$ is selected from F, Cl, Br, I, NO$_2$, Me, i-Pr, Ph, COOH, t-Bu, OCH$_3$, and COOCH$_3$; p is an integer from 0-5, and pharmaceutically acceptable salts thereof.

In certain embodiments, the AgrA antagonist can have a formula selected from the group consisting of:

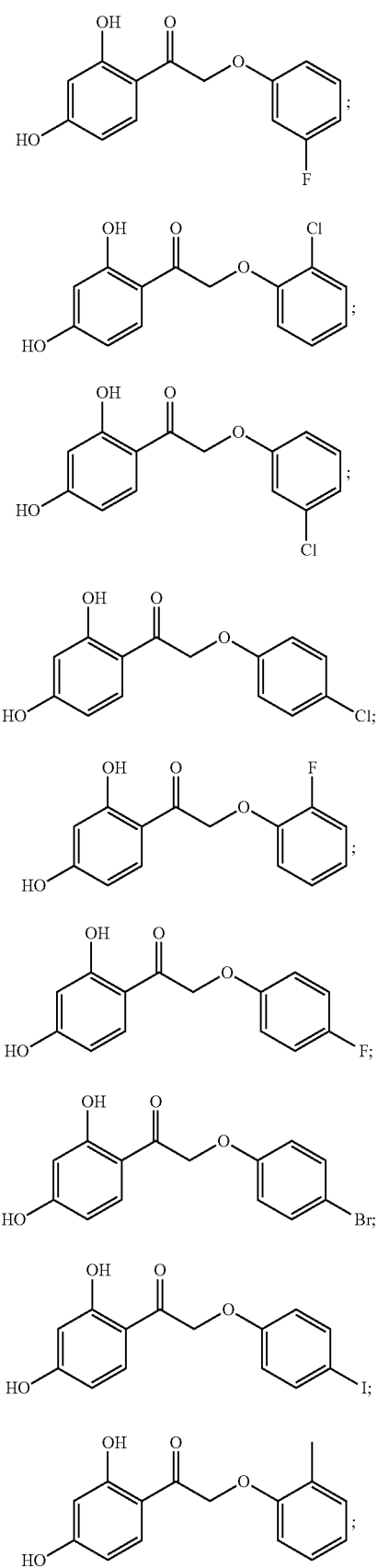
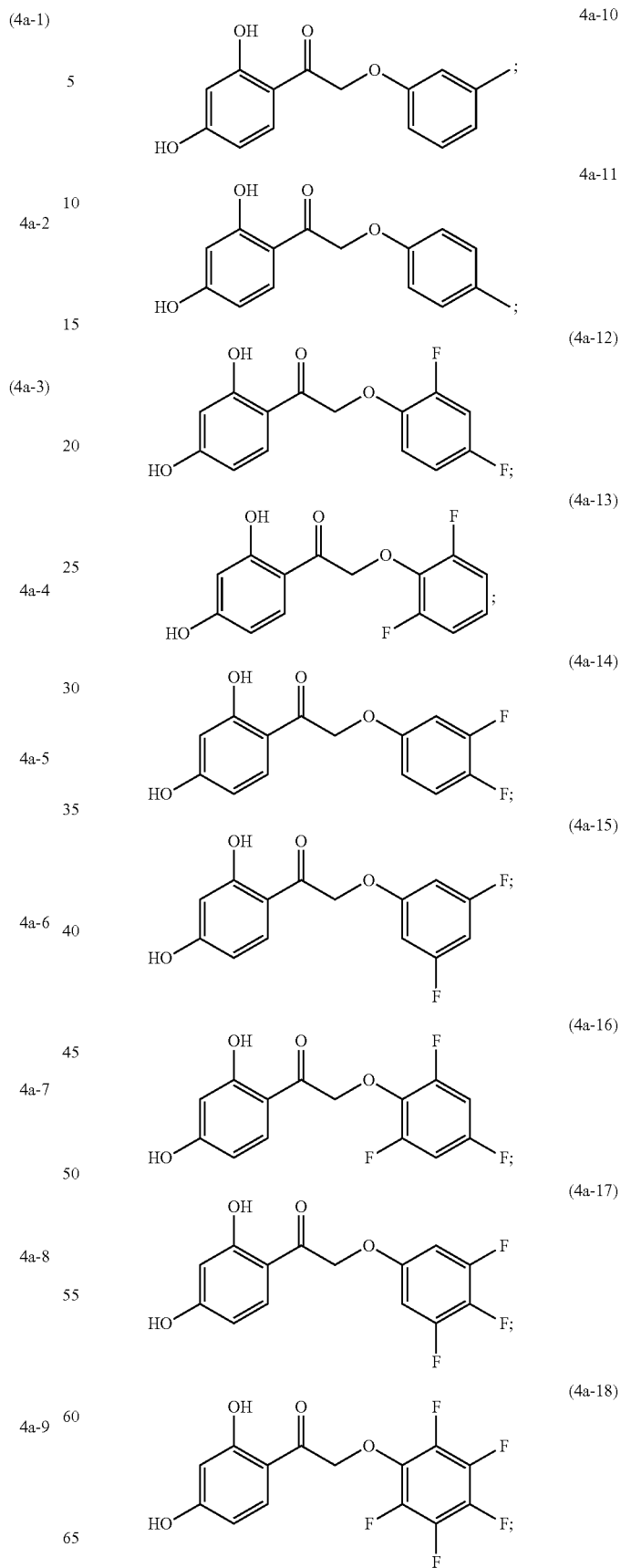

-continued

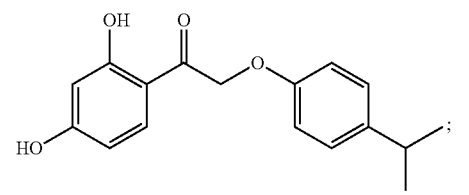
4a-19

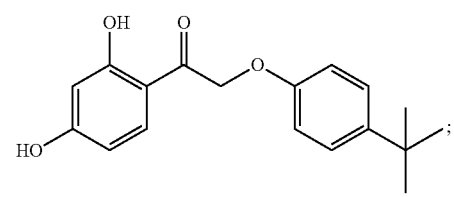
4a-20

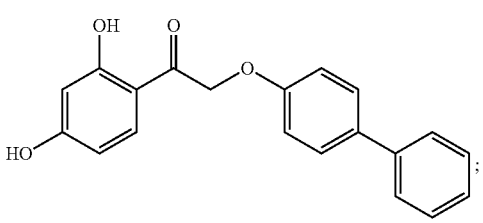
4a-21

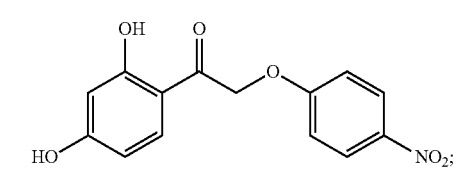
4a-22

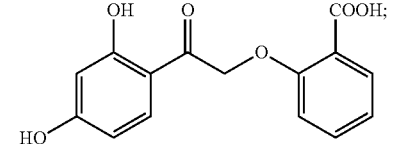
4a-23

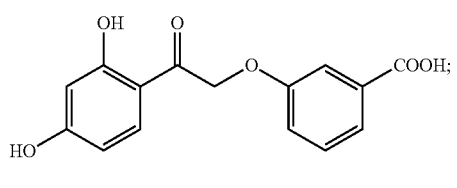
(4a-24)

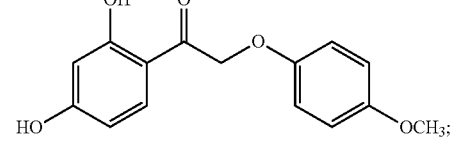
4a-26

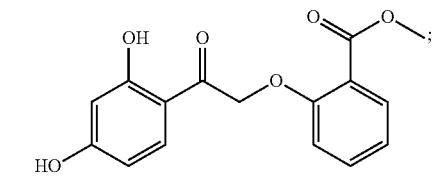
4a-27

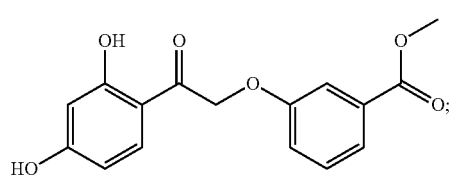
(4a-28)

-continued

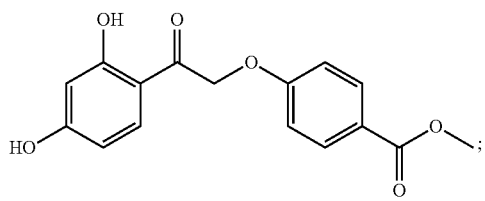
4a-29

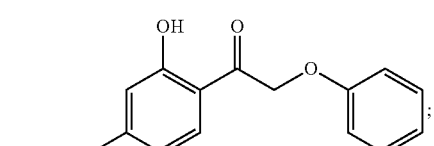
4a-0 and pharmaceutically acceptable salts thereof.

In some embodiments, the AgrA antagonist can include the general formula (4b):

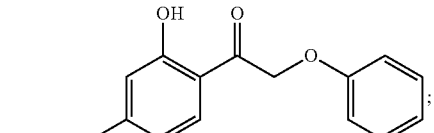
(4b)

wherein $R_6$ is selected from F, Cl, Br, I, $NO_2$, Me, i-Pr, Ph, COOH, t-Bu, $OCH_3$, and $COOCH_3$; p is an integer from 0-5, and pharmaceutically acceptable salts thereof.

In certain embodiments, the AgrA antagonist can include a formula selected from the group consisting of:

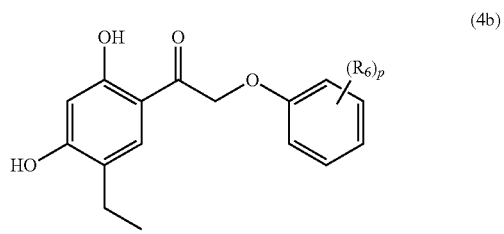
(4b-1)

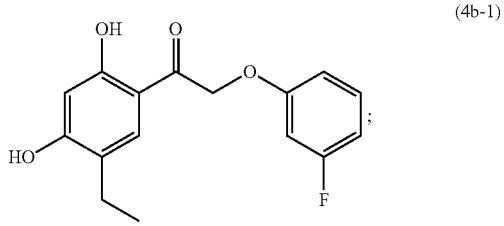
(4b-2)

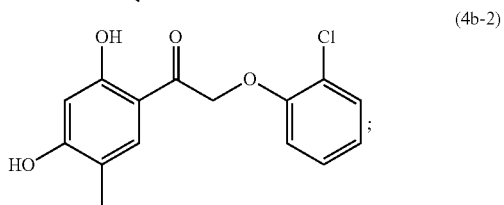
(4b-3)

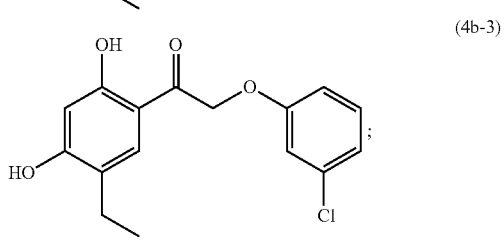

-continued
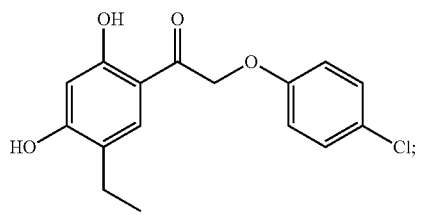 4b-4
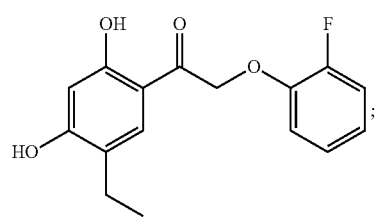 4b-5
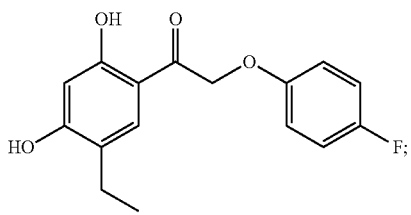 4b-6
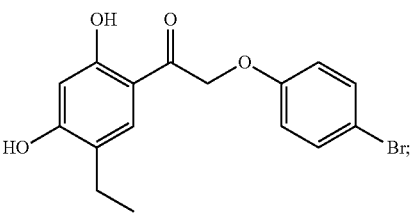 (4b-7)
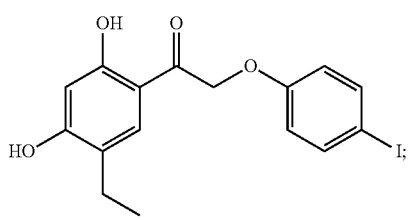 4b-8
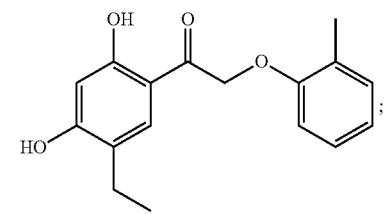 (4b-9)
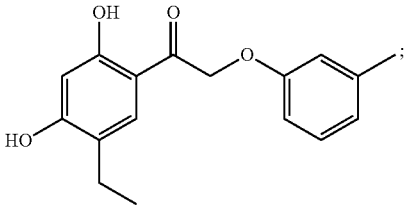 (4b-10)
-continued
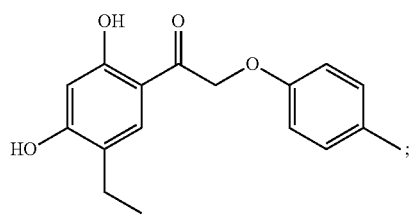 (4b-11)
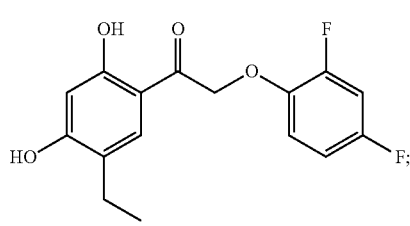 (4b-12)
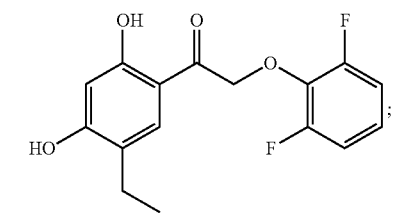 (4b-13)
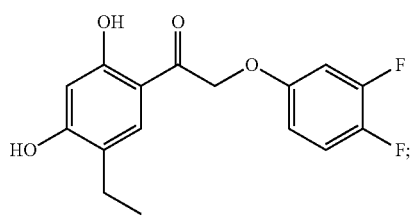 (4b-14)
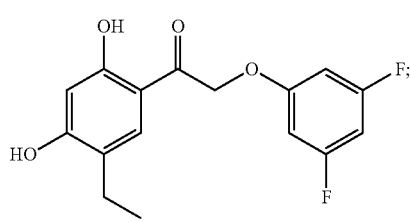 (4b-15)
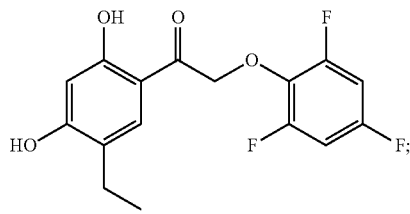 (4b-16)
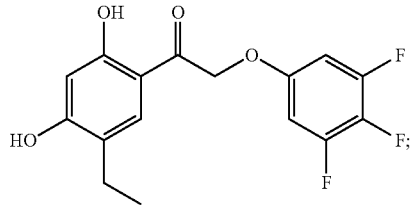 (4b-17)

(4b-18)
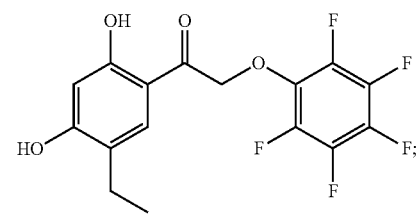

(4b-19)
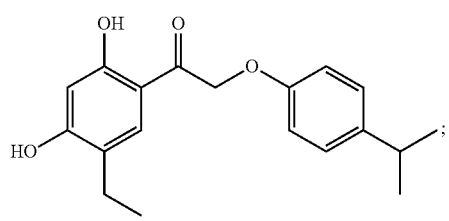

(4b-20)
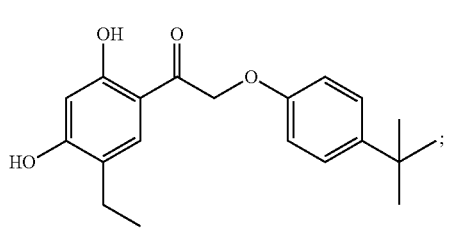

4b-21
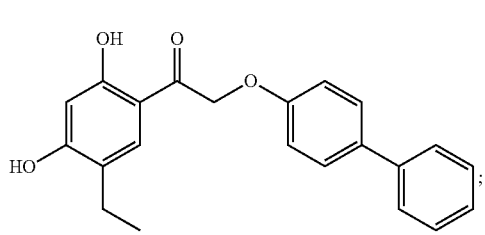

4b-22
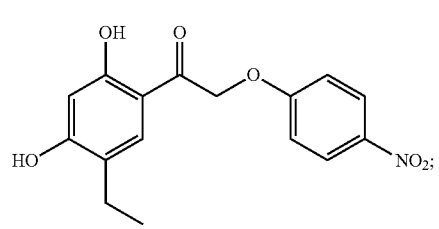

(4b-23)
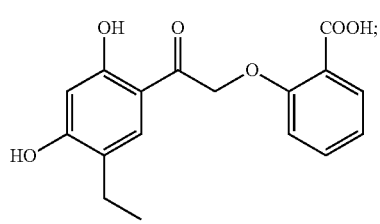

(4b-24)
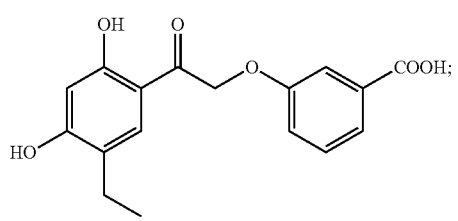

(4b-26)
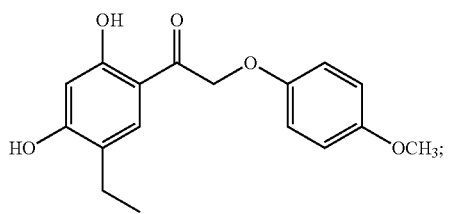

(4b-27)
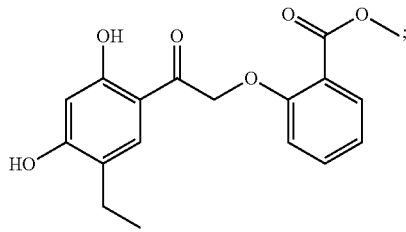

(4b-28)
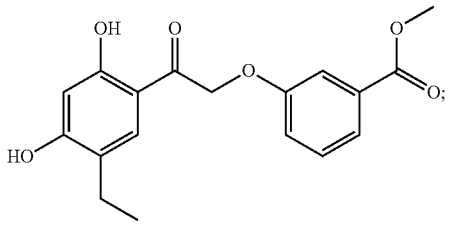

(4b-29)
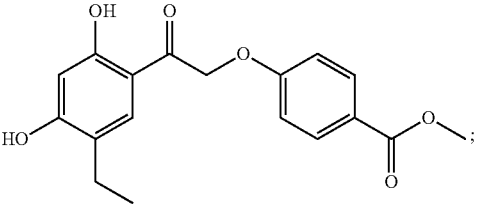

4b-0
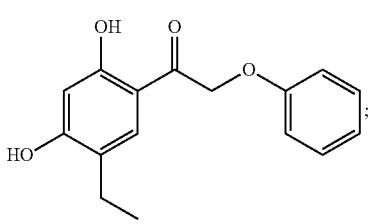

and pharmaceutically acceptable salts thereof.

In some embodiments, the AgrA antagonist can include the general formula (4c):

(4c)
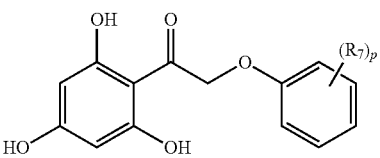

wherein $R_7$ is selected from F, Cl, Br, I, $NO_2$, Me, i-Pr, Ph, COOH, t-Bu, $OCH_3$, and $COOCH_3$; p is an integer from 0-5, and pharmaceutically acceptable salts thereof.

In certain embodiments, the AgrA antagonist can include a formula selected from the group consisting of:

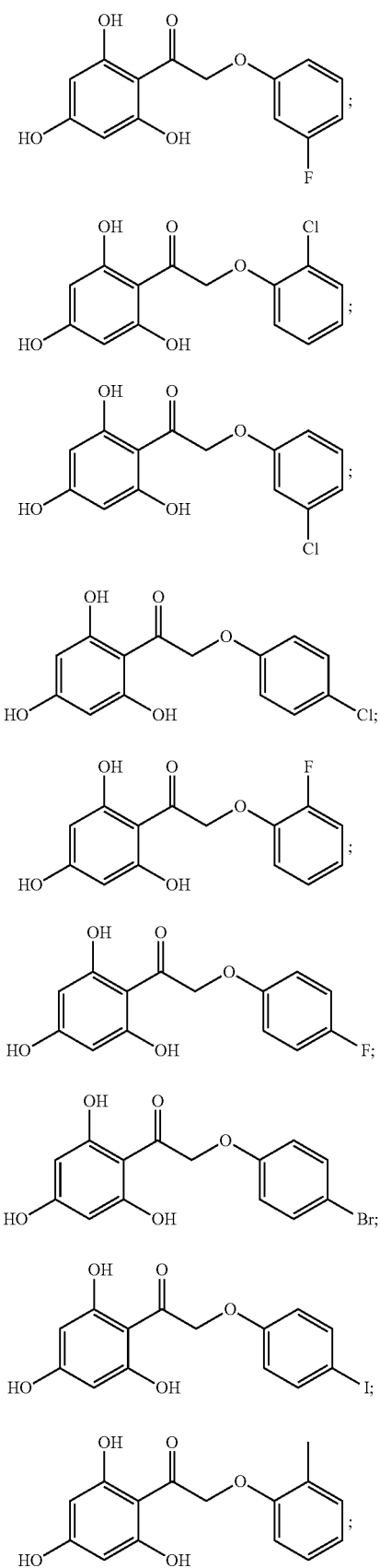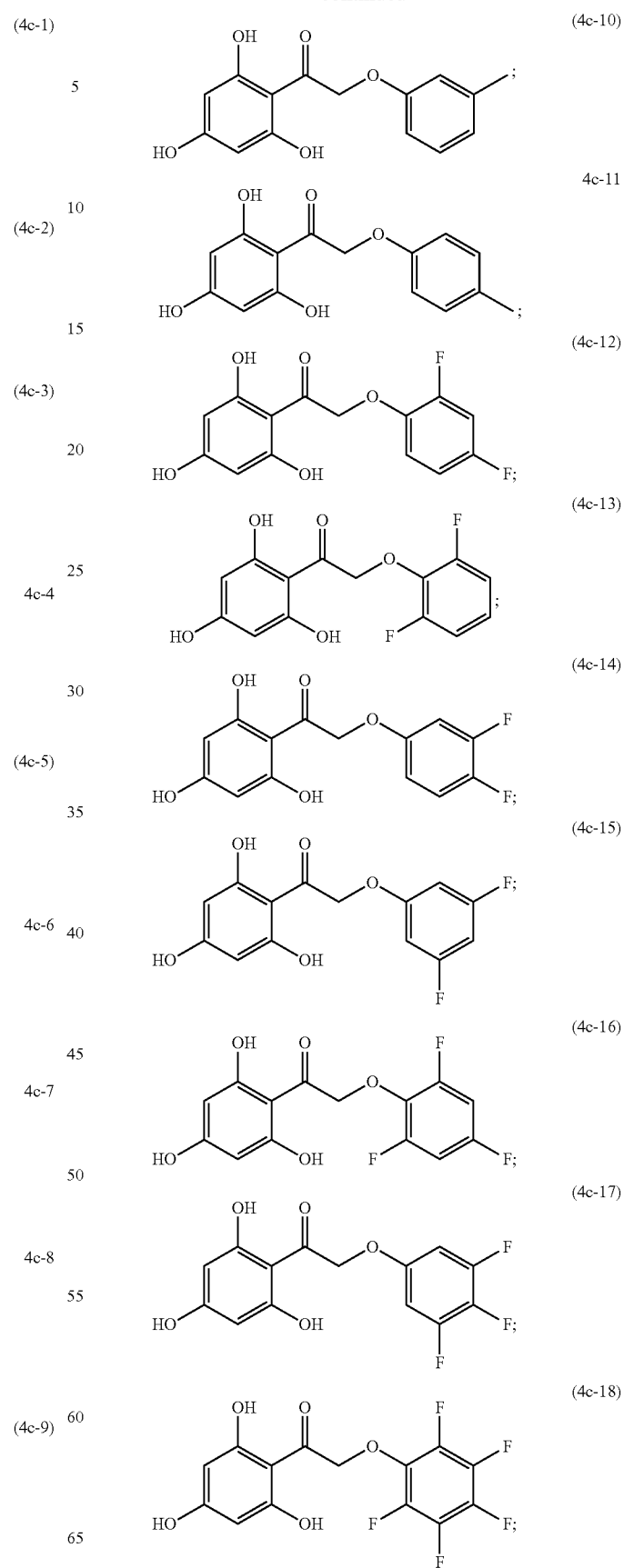

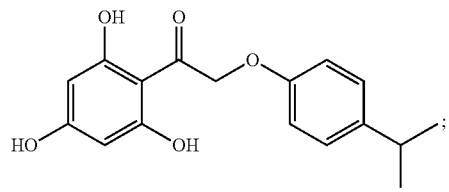
4c-19

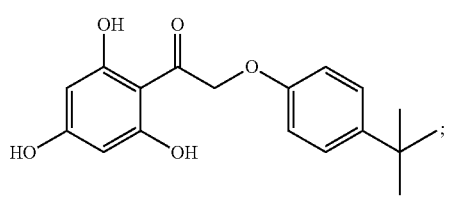
(4c-20)

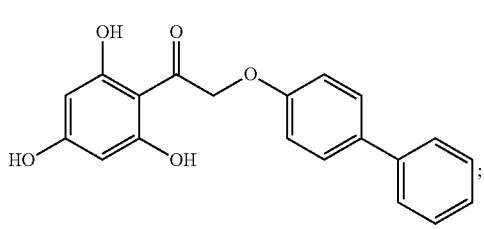
(4c-21)

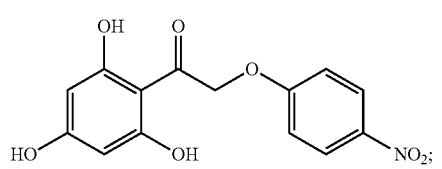
4c-22

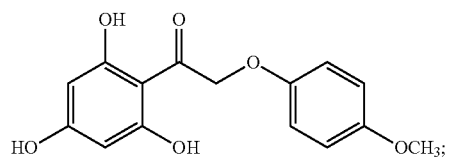
4c-26

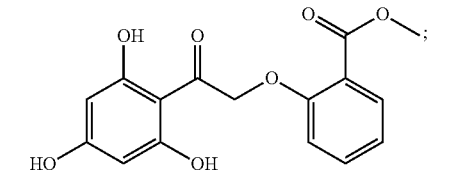
4c-27

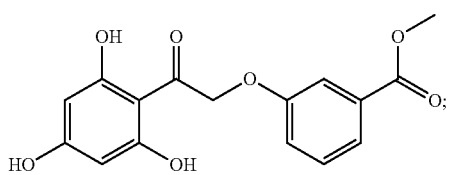
(4c-28)

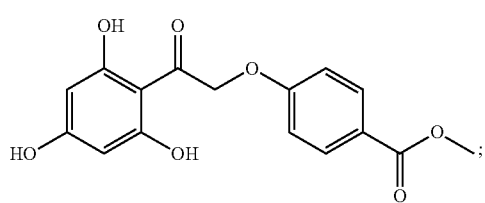
4c-29

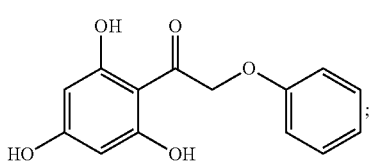
4c-0 and pharmaceutically acceptable salts thereof.

In some embodiments, the AgrA antagonist include the general formula (4d):

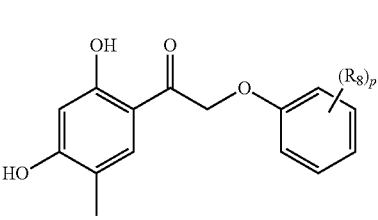
(4d)

wherein $R_8$ is selected from F, Cl, Br, I, $NO_2$, Me, i-Pr, Ph, COOH, t-Bu, $OCH_3$, and $COOCH_3$; p is an integer from 0-5, and pharmaceutically acceptable salts thereof.

In certain embodiments, the AgrA antagonist can include a formula selected from the group consisting of:

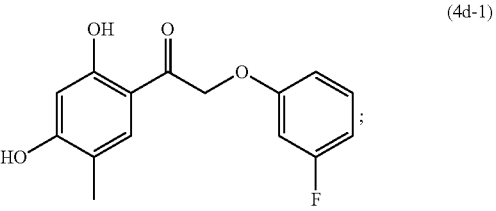
(4d-1)

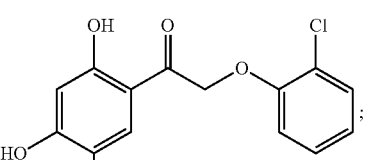
(4d-2)

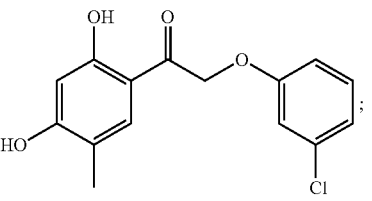
(4d-3)

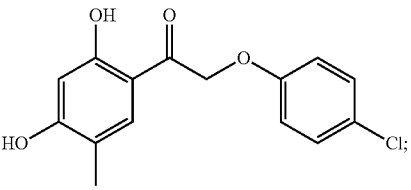
(4d-4)

-continued
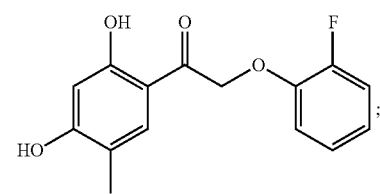 (4d-5)
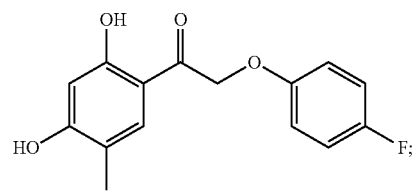 4d-6
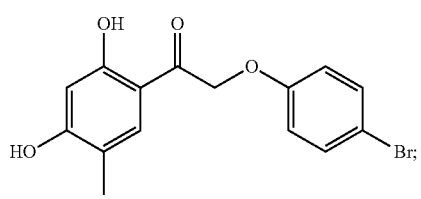 (4d-7)
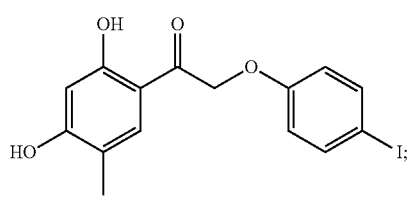 (4d-8)
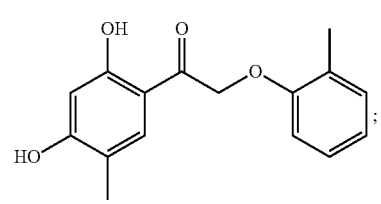 (4d-9)
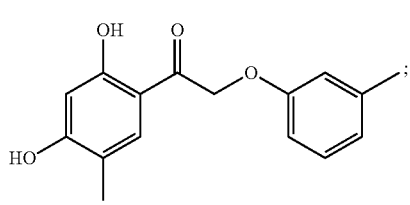 (4d-10)
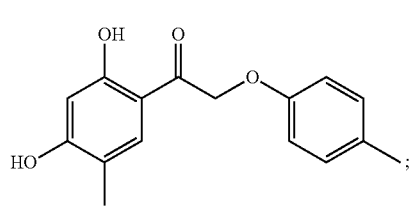 4d-11
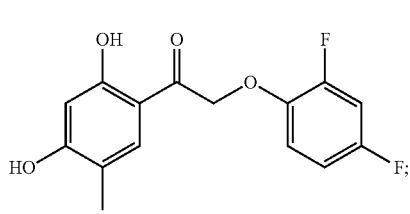 (4d-12)
-continued
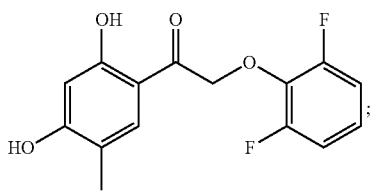 (4d-13)
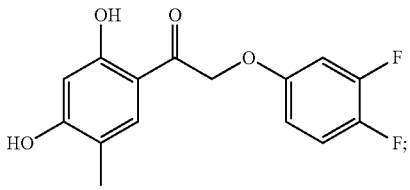 (4d-14)
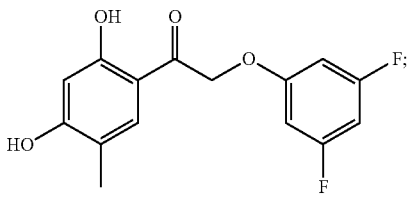 (4d-15)
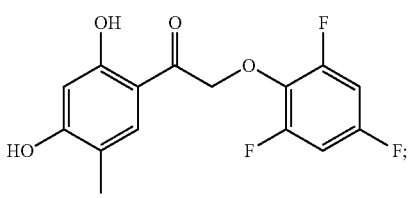 (4d-16)
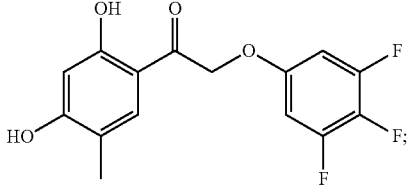 (4d-17)
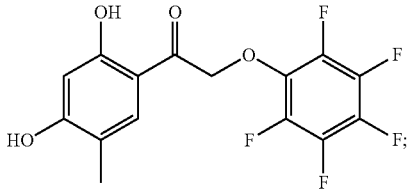 (4d-18)
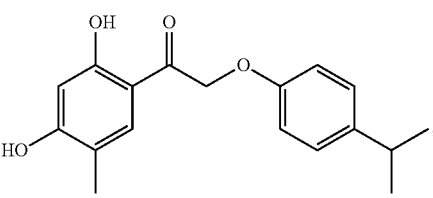 (4d-19)
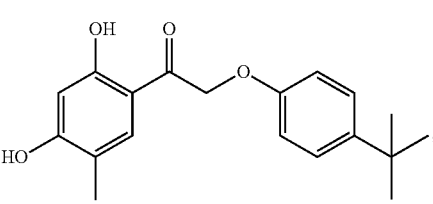 (4d-20)

-continued (4d-21) 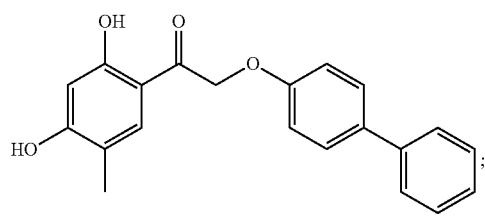

(4d-22) 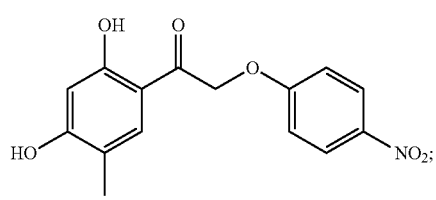

(4d-25) 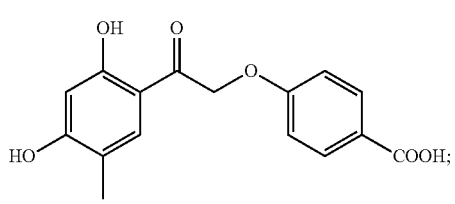

(4d-26) 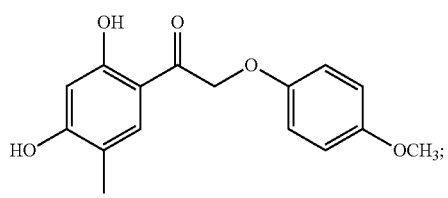

(4d-27) 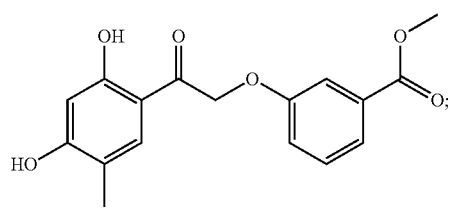

(4d-28)

(4d-29)

-continued (4d-0) 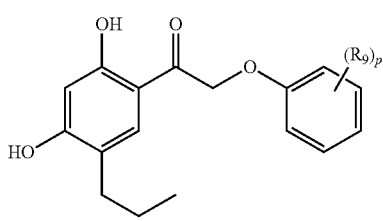

and pharmaceutically acceptable salts thereof.

In some embodiments, the AgrA antagonist can include the general formula (4e):

(4e)

wherein $R_9$ is selected from F, Cl, Br, I, $NO_2$, Me, i-Pr, Ph, COOH, t-Bu, $OCH_3$, and $COOCH_3$; p is an integer from 0-5, and pharmaceutically acceptable salts thereof.

In certain embodiments, the AgrA antagonist can include a formula selected from the group consisting of:

4e-1 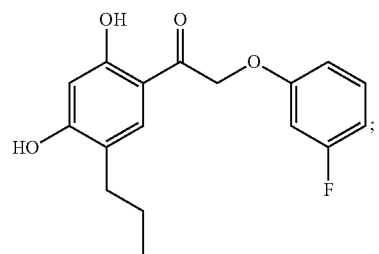

4e-2 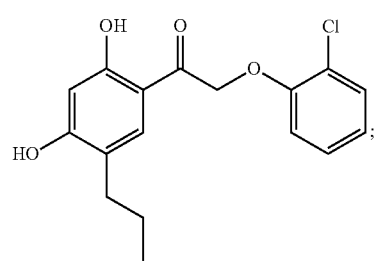

4e-4 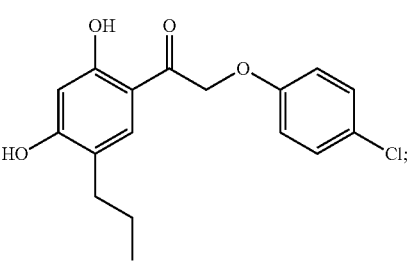

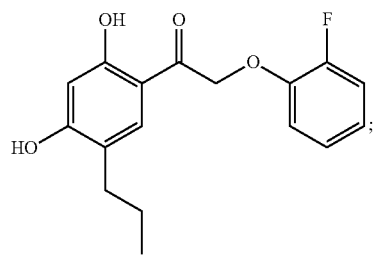
4e-5
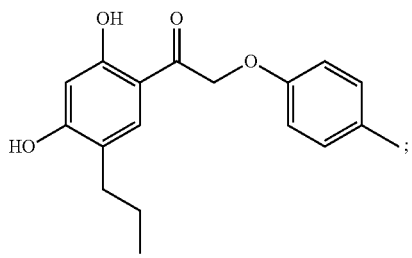
4e-11
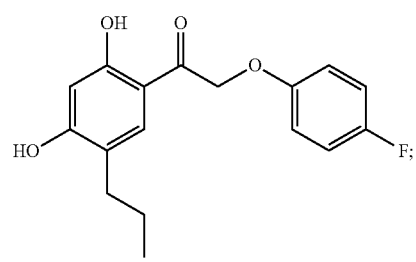
4e-6
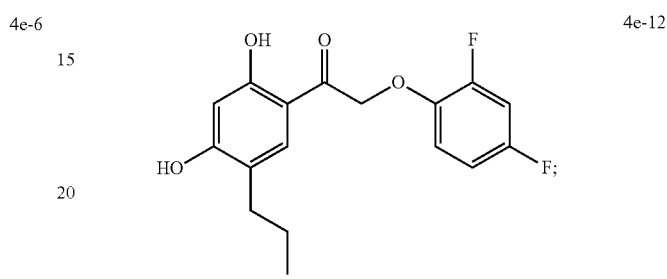
4e-12
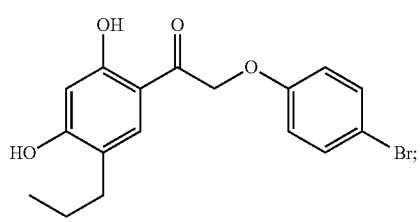
4e-7
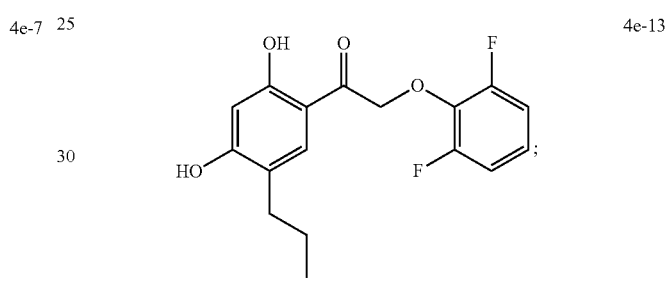
4e-13
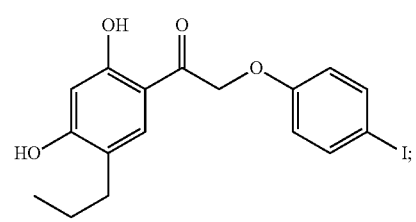
4e-8
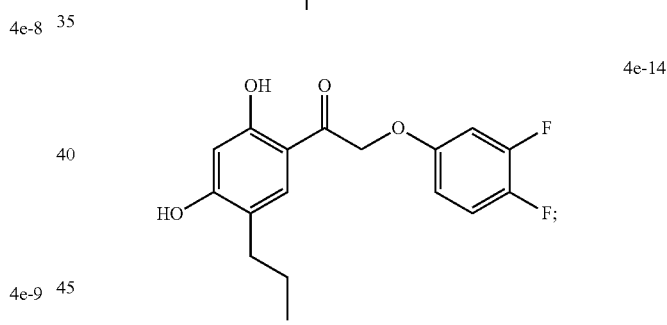
4e-14
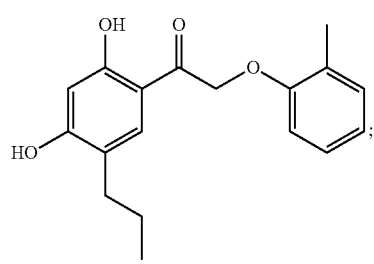
4e-9
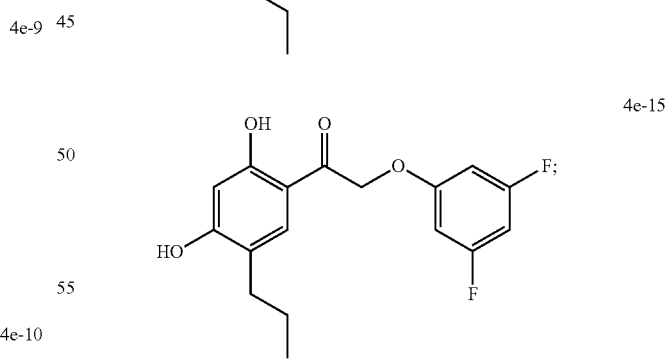
4e-15
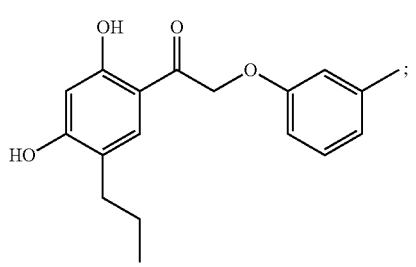
4e-10
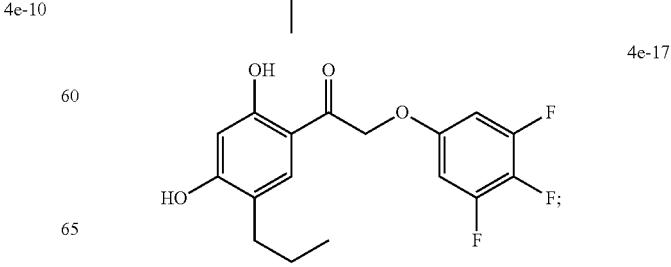
4e-17

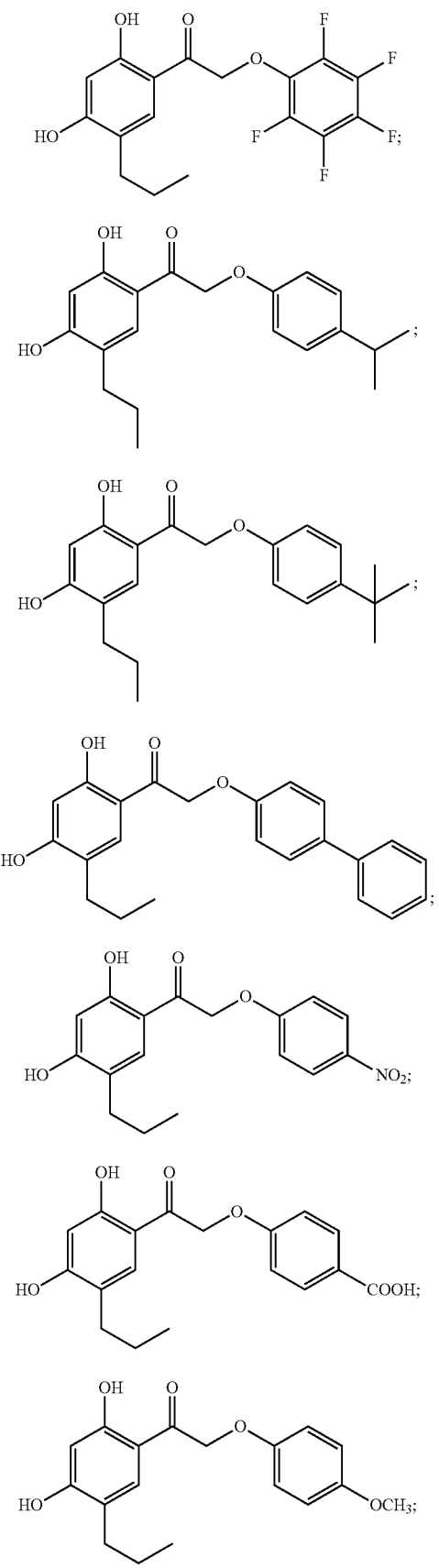
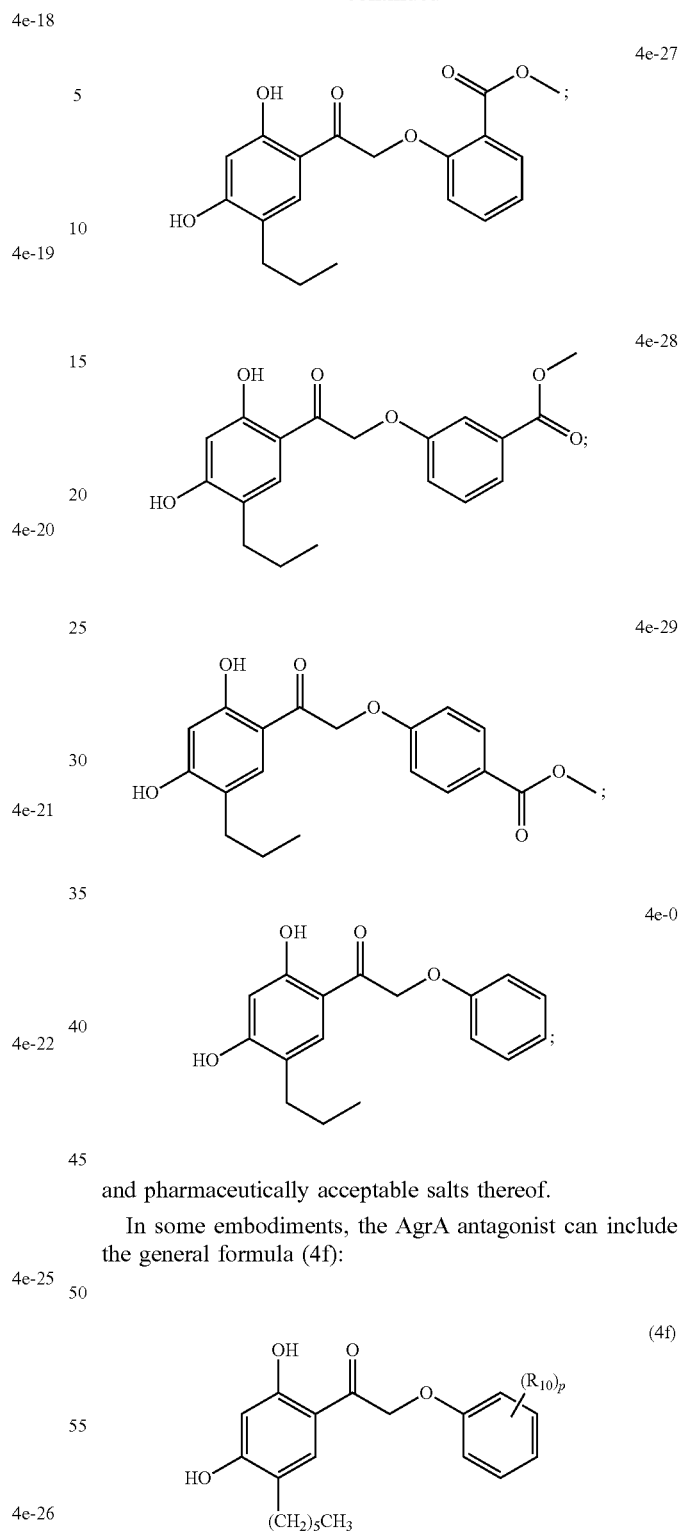

and pharmaceutically acceptable salts thereof.

In some embodiments, the AgrA antagonist can include the general formula (4f):

wherein $R_{10}$ is selected from F, Cl, Br, I, $NO_2$, Me, i-Pr, Ph, COOH, t-Bu, $OCH_3$, and $COOCH_3$; p is an integer from 0-5, and pharmaceutically acceptable salts thereof.

In certain embodiments, the AgrA antagonist can include a formula selected from the group consisting of:

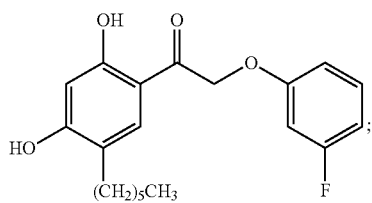

4f-1

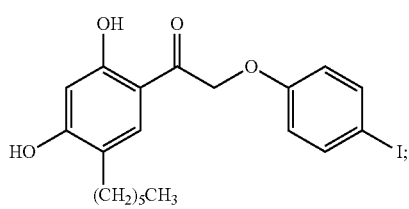

4f-8

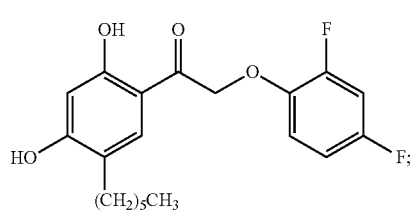

4f-12

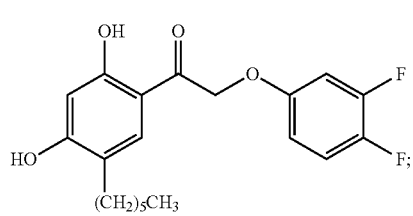

4f-14

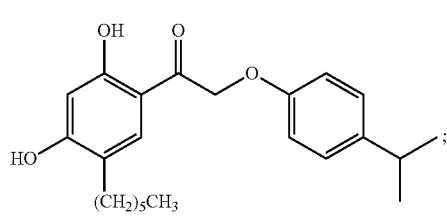

4f-19

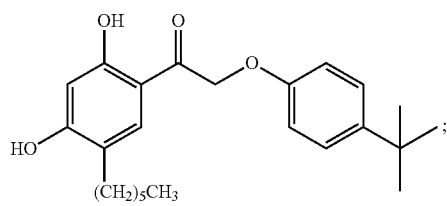

4f-20

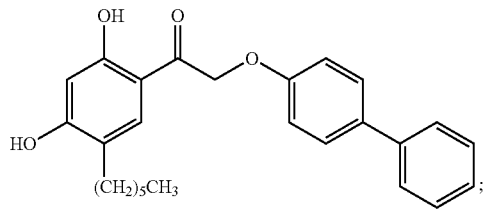

4f-21

-continued

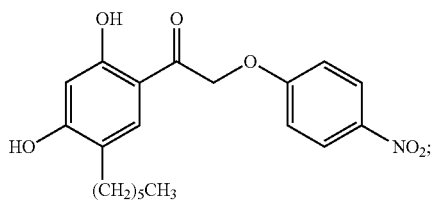

4f-22

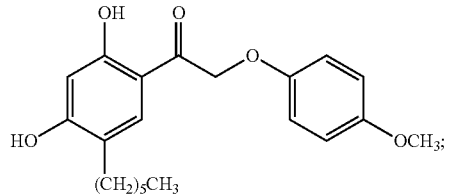

4f-26

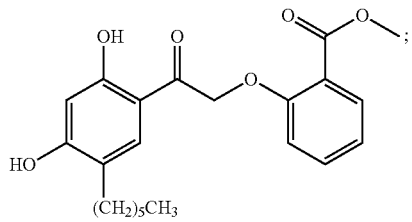

4f-27

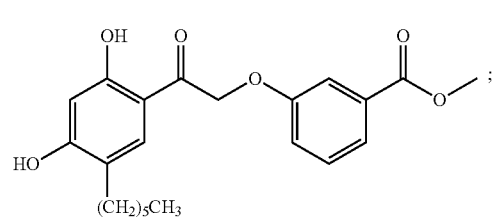

4f-28

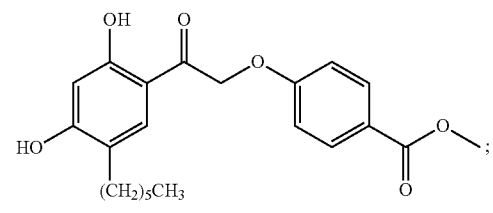

4f-29

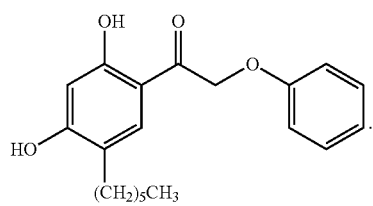

4f-0

As shown in the Examples below compounds 4f-12, 4e-20, 4f-29, 4e-14, 4f-28, 4e-15, 4e-12, 4e-17, 4f-14, 4e-10, 4e-9, 4e-2, 4e-19, 4d-20, 4e-21, 4f-26, 4e-13, 4e-8, 4d-19, 4e-4, 4e-6, 4f-21, 4e-5, and 4e-1 exhibited greater inhibition of rabbit blood hemolysis at 1 μg/mL compared to the anti-virulence agent diflunisal (marketed under the tradename DOLOBID, Merck and Co.) without affecting the growth of the bacteria.

Therefore, in some embodiments, the AgrA antagonist can include a formula selected from the group consisting of:

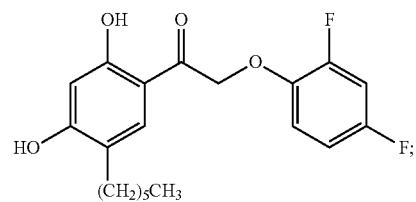
4f-12
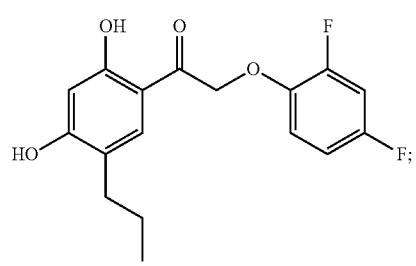
4e-12
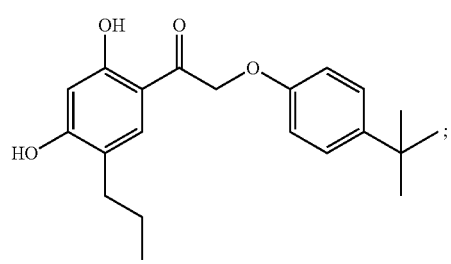
4e-20
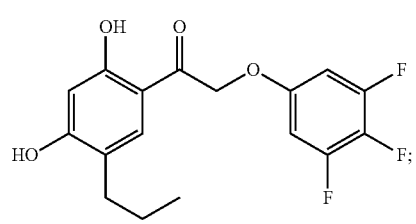
4e-17
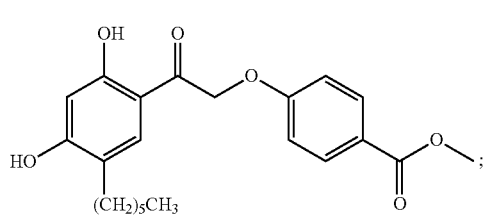
4f-29
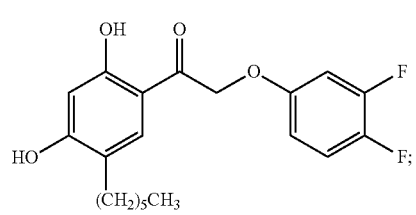
4f-14
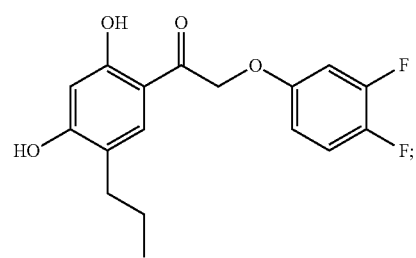
4e-14
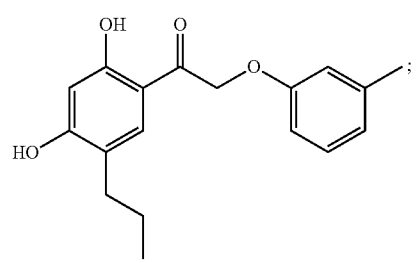
4e-10
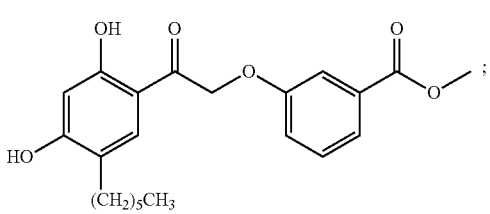
4f-28
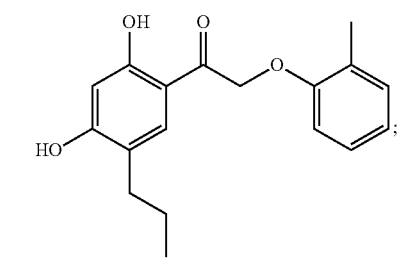
4e-9
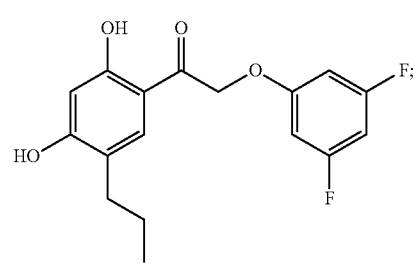
4e-15
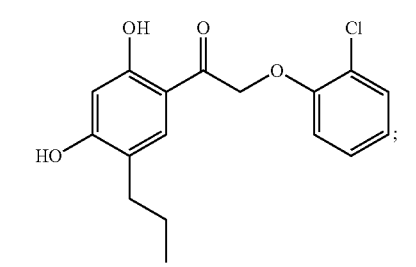
4e-2

-continued

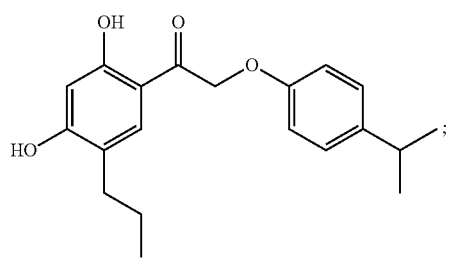
4e-19

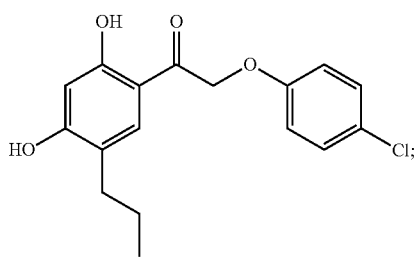
4e-4

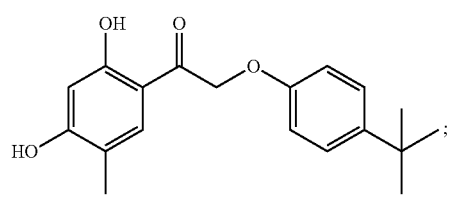
(4d-20)

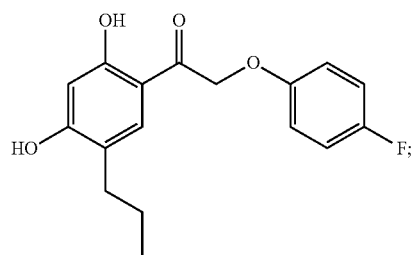
4e-6

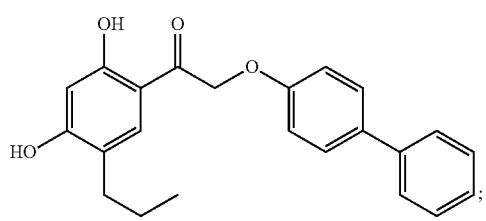
4e-21

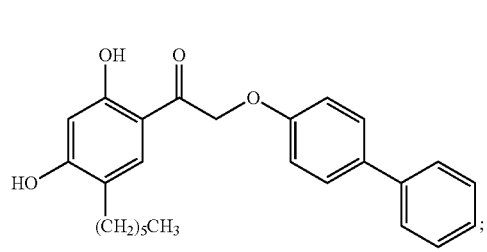
4f-21

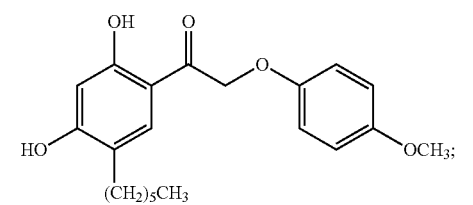
4f-26

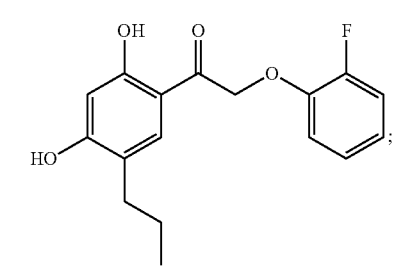
4e-5

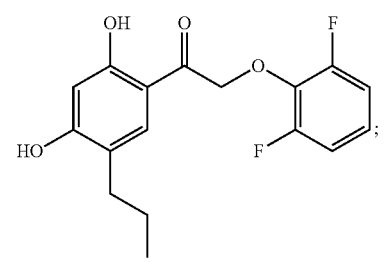
4e-13

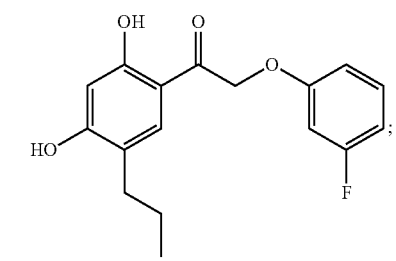
4e-1

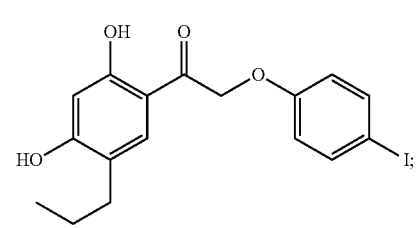
4e-8

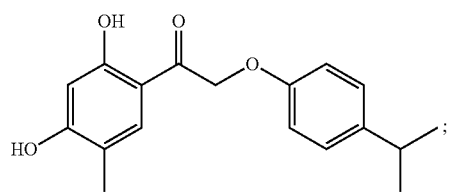
4d-19 and pharmaceutically acceptable salts thereof.

As shown in the Example below, five compounds (i.e., compounds indentified in Table 1 as 4f-12, 4e-20, 4f-29, 4e-14 and 4f-28) were found to substantially inhibit (by at least 90%) hemolysis of erythrocytes in defibrinated rabbit blood at a concentration of 1 µg/ml in the presence of Staphylococcus aureus (MRSA strain USA3000) without affecting the growth of the bacteria. Therefore, in certain embodiments, the AgrA antagonist can include a formula selected from the group consisting of:

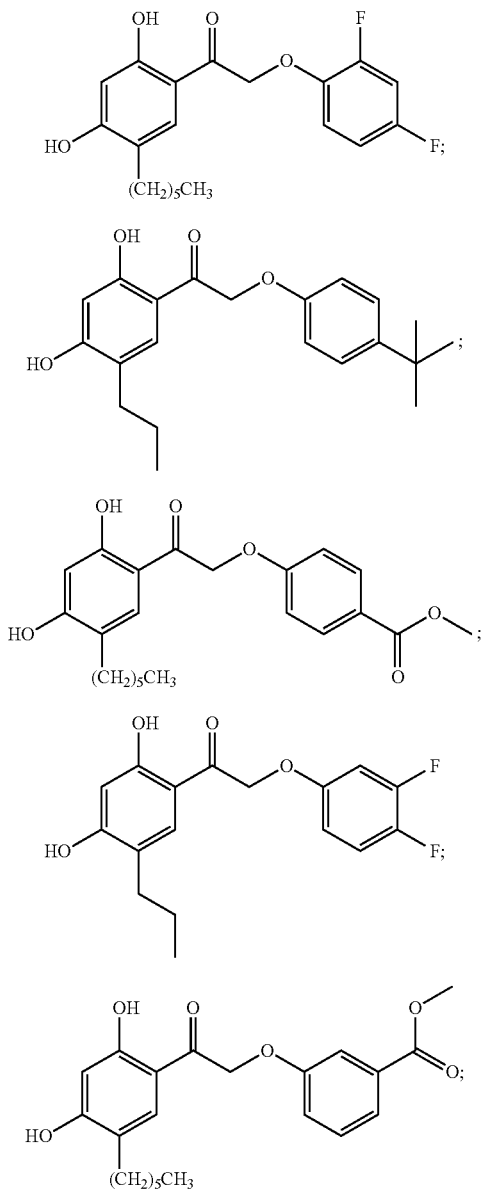

and pharmaceutically acceptable salts thereof.

Additional AgrA antagonists for use in methods described herein can be identified by screening compounds for the ability to inhibit AgrA activity. Of particular interest is the screening of compounds that have a low toxicity for human cells and/or high specificity for gram positive bacteria, such as *Staphylococcus* and *Streptococcus*, preferably with substantially little or no pressure for selection of strains resistant to the action of the compound, and without substantially affecting normal flora of the host subject (e.g., as distinguished from wide-spectrum antibiotics). Toxicity may be quantified in a simple assay wherein bacteria are left to grow planktonic in the absence or presence of various concentrations of a test compound. In such assays, it is contemplated that the concentration of a test compound would be about 1 mg/L, about 5 mg/L, about 10 mg/L, about 20 mg/L, about 50 mg/L and/or about 100 mg/L.

Candidate antagonists of ArgA can be screened for function by a variety of techniques known in the art and/or disclosed within the instant application, such as an ELISA for α-hemolysin. Candidate compounds may be screened individually, in combination, or as a library of compounds.

Candidate compounds screened include chemical compounds. In some aspects of the application, the candidate compound is a small organic molecule having a molecular weight of more than about 50 and less than about 2,500 daltons. Compounds screened are also found among biomolecules including, but not limited to: peptides, saccharides, fatty acids, steroids, pheromones, purines, pyrimidines, derivatives, structural analogs or combinations thereof. The compounds screened can include functional groups necessary for structural interaction with proteins, particularly hydrogen bonding, and typically include at least an amine, carbonyl, hydroxyl, or carboxyl group. In some embodiments, the screened compounds can include biaryl and naphthalene derivatives that have a similar structure to previous identified compounds.

Candidate compounds are obtained from a wide variety of sources including libraries of synthetic or natural compounds. Compounds to be screened can be produced, for example, by bacteria, yeast or other organisms (e.g., natural products), produced chemically (e.g., small molecules, including peptidomimetics), or produced recombinantly. It is further contemplated that natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

In many drug screening programs, with test libraries of compounds and natural extracts, high throughput assays are desirable in order to maximize the number of compounds surveyed in a given period of time. Assays of the present invention may be developed with purified or semi-purified proteins or with lysates. These assays are often preferred as "primary" screens in that they can be generated to permit rapid development and relatively easy detection of an alteration in a molecular target, which is mediated by a test agent. Assays of the present invention can include cell-based assays. Cell-based assays may be performed as either a primary screen, or as a secondary screen to confirm the activity of compounds identified in a cell free screen, such as an in silico screen.

This application also relates to a method of screening in silico for a compound effective in blocking phosphorylation of an AgrA N-terminal phosphoryl-binding pocket centered on residue Asp 59. For example, a 3-D model of the N-terminal regulatory domain of AgrA can be built using the 3-D structure of a homologous protein. The sequence of AgrA N terminal domain (AgrA N) can be compared against the protein sequences in the Protein Data Bank using a BLAST search to identify a homologous protein. In some aspects, the degree of sequence identity of the homologous protein is greater than about 20%. An initial model can then be generated using a suitable protein modeling software program. In some aspects, the model can then be subjected to energy refinement with software program CNS.

Once a model is built, small molecule AgrA antagonists that block the N-terminal phosphoryl-binding pocket of AgrA centered on Asp 59 can be determined by methods well known in the relevant art using in silico conformation screening techniques. In one example, virtual screening of the National Cancer Institute-Frederick Scientific (NCI) Library of small molecules, downloaded from the publicly available ZINC database, can be performed using a multiprocessor Linux-based workstation with drug discovery software (e.g., program GLIDE within the drug discovery software suite from Schrödinger LLC. (Portland, Oreg.)).

In some aspects, candidate compounds, including those collected from an in silico similarity search, may be further screened for efficacy using in vitro and/or in vivo experimental screening methods described herein. The efficacy of an identified compound can be assessed by generating dose response curves from data obtained using various concentrations of the test compound. Moreover, a control assay can also be performed to provide a baseline for comparison. Such candidates can be further tested for their ability to: inhibit phosphorylation of the AgrA Asp 59 residue in vitro; inhibit AgrA C-terminal DNA binding activity in vitro; inhibit AgrA transcription factor activity in vitro; inhibit the synthesis of one or more virulence factors by a bacterium (e.g., *Staphylococcus* and/or *Streptococcus* bacterium) in vitro; reduce the virulence of a bacterium (e.g., *Staphylococcus* and/or *Streptococcus* bacterium) in vitro or in vivo; and/or for other properties, such as the ability to protect in vivo against bacterial infection.

In one particular embodiment, as shown in the Examples below, a candidate compound can be assayed in vitro for efficacy against virulence in *Staphylococcus aureus* MRSA strain USA300 by measuring rabbit blood hemolysis inhibition in vitro.

In some aspects, the efficacy of the compound can be tested in vivo in animal models. Compounds having a desired activity as determined in the assays described above can be further screened for their ability to affect bacterium (e.g., *Staphylococcus* and/or *Streptococcus* bacterium) virulence factor production, and to affect bacterial infection, in a non-human animal model. The animal model selected will vary with a number of factors including, but not limited to, the particular pathogenic strain of bacteria (e.g., MRSA USA300) against which candidate compounds are to be screened, the ultimate subject for which the candidate compounds are to serve as therapeutics, etc. Animals that can be used in screening assays include any animal susceptible to infection by the selected bacteria species. For example, where the *Staphylococcus* species is *S. aureus*, the animal model can be a rodent model, preferably a mouse model.

In general, the candidate compound is administered to a non-human animal susceptible to bacterial infection, where the animal has been previously infected with the bacterium or receives an infectious dose of the bacterium in conjunction with the candidate compound. The candidate compound can be administered in any manner desired and/or appropriate for delivery of the compound in order to affect a desired result. For example, the candidate compound can be administered by injection (e.g., by injection intravenously, intramuscularly, subcutaneously, or directly into the tissue in which the desired affect is to be achieved), topically, orally, or by any other desirable means. Normally, this screen will involve a number of animals receiving varying amounts and concentrations of the candidate compounds (from no compound to an amount of compound that approaches an upper limit of the amount that can be delivered successfully to the animal), and may include delivery of the compound in different formulations. The compounds can be administered singly or can be combined in combinations of two or more, especially where administration of a combination of compounds may result in a synergistic effect.

The effect of compound administration upon the animal model can be monitored by any suitable method, such as assessing the number and size of bacteria-associated lesions, overall health, survival rate, etc. Where the candidate compound affects bacterial infection in a desirable manner (e.g., by reducing infectious load, facilitating lesion regression, extending lifetime, etc.), the candidate compound is identified as an effective compound for use in the treatment of bacterial infection and related diseases and disorders in a subject.

The AgrA antagonists described herein can be provided in a pharmaceutical composition. The pharmaceutical composition can further include a conventional pharmaceutical carrier or excipients, an be provided in solid, semi-solid, liquid or aerosol dosage forms, such as, for example, tablets, capsules, powders, liquids, gels, suspensions, suppositories, aerosols or the like. In addition, these compositions may include additional active therapeutic agents, adjuvants, etc.

For example, pharmaceutical compositions can contain pharmaceutically acceptable carriers, such as excipients and auxiliaries that facilitate processing of the AgrA antagonists into compositions that can be used pharmaceutically. The pharmaceutical compositions can be manufactured in a known manner, such as by conventional mixing, granulating, dragee-making, dissolving, lyophilizing processes, and the like. For example, pharmaceutical compositions for oral use can be obtained by combining the AgrA antagonists described herein with solid excipients, optionally grinding the resulting mixture, and processing the mixture of granules after adding auxiliaries (if desired or necessary) to obtain tablets or dragee cores.

Excipients that can be used as part of the pharmaceutical composition can include fillers, such as saccharides (e.g., lactose or sucrose), mannitol or sorbitol, cellulose preparations and/or calcium phosphates, for example, tricalcium phosphate or calcium hydrogen phosphate, as well as binders, such as starch paste using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents can be added, such as the above-mentioned starches and also carboxymethyl-starch, cross-linked polyvinyl pyrrolidone, agar, or alginic acid or a salt thereof, such as sodium alginate. Auxiliaries can include flow-regulating agents and lubricants, such as silica, talc, stearic acid or salts thereof, such as magnesium stearate or calcium stearate, and/or polyethylene glycol. Dragee cores can be provided with coatings that, if desired, are resistant to gastric juices. For this purpose, concentrated saccharide solutions can be used, which may optionally contain gum arabic, talc, polyvinyl pyrrolidone, polyethylene glycol, and/or titanium dioxide, lacquer solutions and suitable organic solvents or solvent mixtures. To produce coatings resistant to gastric juices, solutions of suitable cellulose preparations, such as acetylcellulose phthalate or hydroxypropylmethylcellulose phthalate can be used. Slow-release and prolonged-release formulations may be used with particular excipients, such as methacrylic acid-ethylacrylate copolymers, methacrylic acid-ethyl acrylate copolymers, methacrylic acid-methyl methacrylate copolymers, and methacrylic acid-methyl methylacrylate copolymers. Dye stuffs or pigments can be added to the tablets or dragee coatings, for example, for identification or to characterize combinations of active compound doses.

Other pharmaceutical preparations that can be used orally include push-fit capsules made of gelatin, as well as soft, sealed capsules made of gelatin and a plasticizer, such as glycerol or sorbitol. The push-fit capsules can contain the active compounds in the form of granules that may be mixed with fillers, such as lactose, binders, such as starches, and/or lubricants, such as talc or magnesium stearate and, optionally, stabilizers. In soft capsules, the active compounds can be dissolved or suspended in suitable liquids, such as fatty oils or liquid paraffin. In addition, stabilizers may be added.

Examples of formulations for parenteral administration can include aqueous solutions of the active compounds in water-soluble form, for example, water-soluble salts and alkaline solutions. Especially preferred salts are maleate, fumarate, succinate, S,S tartrate, or R,R tartrate. In addition, suspensions of the active compounds as appropriate oily injection suspensions can be administered. Suitable lipophilic solvents or vehicles can include fatty oils, for example, sesame oil, or synthetic fatty acid esters, for example, ethyl oleate or triglycerides or polyethylene glycol-400 (the compounds are soluble in PEG-400). Aqueous injection suspensions can contain substances that increase the viscosity of the suspension, such as sodium carboxymethyl cellulose, sorbitol, and/or dextran. Optionally, the suspension may also contain stabilizers.

It is further contemplated that an AgrA antagonist or pharmaceutical compositions thereof described herein can be used in preventative and therapeutic treatments for infection of pathogenic bacterium, such as *Staphylococcus* or *Streptococcus*. The rationale behind treatment of a subject with an AgrA antagonist is multifaceted. By preventing the synthesis and excretion of virulence factors, the pathogenecity of the invading organism is diminished, or even eliminated. Furthermore, AgrA may itself have an adverse effect on the immune system of the host subject independent of RNAIII. For example, it is contemplated that AgrA antagonist mediated inhibition of phenol-soluble modulins (PSMs), which play a role in the immune evasion of *S. aureus*, can provide a beneficial effect.

Therefore, another aspect described herein relates to a method of treating a bacterial infection in a subject. The method includes administering to the subject an amount of an AgrA antagonist effective to inhibit synthesis of one or more virulence factors by a bacterium.

An AgrA antagonist or pharmaceutical compositions thereof described herein can be used to prevent or treat infection of a subject by any bacteria species that utilizes the AgrA response regulator in quorum sensing and the production of virulence factors. The AgrA antagonists are typically administered to subjects having or at risk of having a bacterial infection (e.g., *Staphylococcus* and/or *Streptococcus* infection). For example, a subject that can benefit from treatment with an AgrA antagonist described herein can be a hospital patient at risk of developing nosocomial infection or a subject known to be infected with or having been exposed to antibiotic resistant bacteria such as, for example, Methicillin-resistant *S. aureus*, Vancomycin-intermediary-sensible *S. aureus*, and Vancomycin-resistant *S. aureus*. Methods of detecting the presence of a *Staphylococcus* bacterial infection are well known, for example, by culturing from a sample from the subject, e.g. a blood culture, can be used.

In another aspect, an AgrA antagonist or pharmaceutical composition thereof described herein can be administered to a subject to inhibit the activity of AgrA thereby preventing the production of virulence factors that aid in bacterial infection or development of a disease condition or disorder associated with the bacterial infection. Examples of diseases and disorders associated with a bacterial infection responsive to AgrA antagonist treatment can include, without limitation, postoperative wound infections, bacteraemia, septic arthritis, pneumonia, osteomyelitis, meningitis, mastitis, erysipelas, cellulitis, sepsis, acute endocarditis, furuncles, carbuncles, superficial abscesses, deep abscesses in various organs, impetigo, food poisoning, gastroenteritis, urinary tract infection, toxic shock syndrome, and scalded skin syndrome.

Pharmaceutical compositions including AgrA antagonists can be administered to a subject at a therapeutically effective dosage, e.g., a dosage sufficient to improve the chance of successful prevention or treatment of infection or related disease or disorder. Generally, depending on the intended mode of administration, the pharmaceutically acceptable composition will contain about 0.1% to 100 wt. %, preferably about 0.5% to about 50%, by weight of active compound, the remainder being suitable pharmaceutical excipients, carriers, etc. Actual methods for preparing such dosage forms are known, or will be apparent, to those skilled in this art. For example, see Remington the Science and Practice of Pharmacy, $21^{th}$ ed., Lippincott Williams & Wilkins (2005). Any of the foregoing pharmaceutical compositions may be appropriate in methods in accordance with the present invention, provided that the AgrA antagonist in the composition is not inactivated by the composition and the composition is physiologically compatible.

The pharmaceutical compositions can be administered to any animal subject that can experience the beneficial effects of an AgrA antagonist described herein. In some aspects the animal subject is a human. The pharmaceutical compositions described herein can be administered by any means that achieve their intended purpose. For example, administration can be by parenteral, topical, local, subcutaneous, oral, intravenous, intraarticular, intrathecal, intramuscular, intraperitoneal, or intradermal delivery, or by transdermal, buccal, oromucosal, ocular routes or via inhalation. In some aspects, administration to a subject is systemic. In other aspects, administration to a subject is local, such as in a topical solution, topical ointment, or topical cream.

An AgrA antagonist or pharmaceutical compound described herein, can be administered prior to a bacterial infection, after infection but prior to the manifestation of symptoms of a disease of disorder associated with the infection, or after the manifestation of symptoms associated with the production of one or more bacterial virulence factors to prevent further bacterial multiplication and to prevent further production of virulence factors thereby hindering development of the disease or its progression.

It will be understood, however, that the total daily usage of the AgrA antagonist in a therapeutic method described herein will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

In another embodiment, an AgrA antagonist can be administered in combination with an antibacterial therapeutic. Exemplary antibacterial therapeutics include, but are not limited to, colloidal silver, penicillin, penicillin G, erythromycin, polymyxin B, viomycin, chloromycetin, streptomycins, cefazolin, ampicillin, methicillin, oxacillin, nafcillin, cloxacillin, dicloxacillin azactam, tobramycin, cephalosporins (including cephalothin, cefazolin, cephalexin, cephradine, cefamandole, cefoxitin, and 3rd-generation cephalosporins), carbapenems (including imipenem, meropenem, Biapenem), bacitracin, tetracycline, doxycycline, gentamycin, quinolines, neomycin, clindamycin, kanamycin, metronidazole, treptogramins (including Quinupristin/dalfopristun (Synercid™)), Streptomycin, Ceftriaxone, Cefotaxime, Rifampin, glycopeptides (including vancomycin, teicoplanin, LY-333328 (Ortivancin), dalbavancin), macrolides (including erythromycin, clarithromycin, azithromycin, lincomycin, and clindamycin), ketolides (including Telithromycin, ABT-773), tetracyclines, glycylcyclines (including Terbutyl-minocycline (GAR-936)), aminoglycosides, chloramphenicol, Imipenem-cilastatin, fluoroquinolones (including ofloxacin, sparfloxacin, gemifloxacin, cinafloxacun (DU-6859a)) and other topoisomerase inhibitors, Trimethoprim-sulfamethoxazole (TMP-SMX), Ciprofloxacin, topical mupirocin, Oxazolidinones (including AZD-2563, Linezolid (ZyvoX™)), Lipopeptides (including Daptomycin, Ramoplanin), ARBELIC (TD-6424) (Theravance), TD6424 (Theravance), isoniazid (INN), rifampin (RIF), pyrazinamide (PZA), Ethambutol (EMB), Capreomycin, cycloserine, ethionamide (ETH), kanamycun, and p-aminosalicylic acid (PAS).

The combination of an AgrA antagonist with one or more additional antibacterial therapeutics in a method and/or composition of the present invention may reduce the amount of either pharmaceutical compound needed as a therapeutically effective dosage, and thereby reduce any negative side effects the agents may induce in vivo. In addition, the combination of an AgrA antagonist with one or more additional antibacterial therapeutics in a method and/or composition described herein may reduce the MIC (minimum inhibitory concentration) of the antibacterial therapeutic, which in turn reduces the opportunity for microbial resistance to specific antibacterial therapeutics. Combination therapies may involve co-administration or sequential administration of the pharmaceutically active components.

In some aspects, treatment with an AgrA antagonist or pharmaceutical composition thereof may precede or follow the treatment with an additional antibacterial therapeutic, including intervals ranging from minutes to weeks. In some aspects, where the AgrA antagonist and the additional antibacterial therapeutic are administered separately (either in separate compositions administered simultaneously or in separate compositions administered at different time intervals), one would generally ensure that a significant period of time did not expire between the times of each delivery, such that the additional antibacterial therapeutic and the AgrA antagonist would still be able to exert an advantageously combined effect. In such instances, it is contemplated that one would administer both therapeutics within about 1, about 2, about 3, about 4, about 5, about 5, about 6, about 7, about 8, about 9, about 10, about 11, about 12, about 13, about 14, about 15, about 16, about 17, about 18, about 19, about 20, about 21, about 22, about 23, about 24, about 36, about 48, or about 72 hours of each other. In one aspect, both therapeutics are administered within about 6-12 hours of each other. In some situations, it may be desirable to extend the time period for treatment significantly.

In another embodiment, an AgrA antagonist or pharmaceutical compositions thereof can be used to reduce the virulence of bacteria on or associated with a medical device by contacting the device with an AgrA antagonist or pharmaceutical composition thereof in an amount effective to inhibit the synthesis of one or more virulence factors by the bacteria. Percutaneous devices (such as catheters) and implanted medical devices (including, but not limited to, pacemakers, vascular grafts, stents, and heart valves) commonly serve as foci for bacterial infection. The tendency of some microorganisms (e.g., *Staphylococcus* bacteria) to adhere to and colonize the surface of the device, promotes such infections, which increase the morbidity and mortality associated with use of the devices.

A medical device according can include any instrument, implement, machine, contrivance, implant, or other similar or related article, including a component or part, or accessory which is: recognized in the official U.S. National Formulary the U.S. Pharmacopoeia, or any supplement thereof; intended for use in the diagnosis of disease or other conditions, or in the cure, mitigation, treatment, or prevention of disease, in humans or in other animals; or, intended to affect the structure or any function of the body of humans or other animals, and which does not achieve any of its primary intended purposes through chemical action within or on the body of human or other animal, and which is not dependent upon being metabolized for the achievement of any of its primary intended purposes.

A medical device can include, for example, endovascular medical devices, such as intracoronary medical devices. Examples of intracoronary medical devices can include stents, drug delivery catheters, grafts, and drug delivery balloons utilized in the vasculature of a subject. Where the medical device comprises a stent, the stent may include peripheral stents, peripheral coronary stents, degradable coronary stents, non-degradable coronary stents, self-expanding stents, balloon-expanded stents, and esophageal stents. The medical device may also include arterio-venous grafts, by-pass grafts, penile implants, vascular implants and grafts, intravenous catheters, small diameter grafts, artificial lung catheters, electrophysiology catheters, bone pins, suture anchors, blood pressure and stent graft catheters, breast implants, benign prostatic hyperplasia and prostate cancer implants, bone repair/augmentation devices, breast implants, orthopedic joint implants, dental implants, implanted drug infusion tubes, oncological implants, pain management implants, neurological catheters, central venous access catheters, catheter cuff, vascular access catheters, urological catheters/implants, atherectomy catheters, clot extraction catheters, PTA catheters, PTCA catheters, stylets (vascular and non-vascular), drug infusion catheters, angiographic catheters, hemodialysis catheters, neurovascular balloon catheters, thoracic cavity suction drainage catheters, electrophysiology catheters, stroke therapy catheters, abscess drainage catheters, biliary drainage products, dialysis catheters, central venous access catheters, and parental feeding catheters.

The medical device may additionally include either arterial or venous pacemakers, vascular grafts, sphincter devices, urethral devices, bladder devices, renal devices, gastroenteral and anastomotic devices, vertebral disks, hemostatic barriers, clamps, surgical staples/sutures/screws/plates/wires/clips, glucose sensors, blood oxygenator tubing, blood oxygenator membranes, blood bags, birth control/IUDs and associated pregnancy control devices, cartilage repair devices, orthopedic fracture repairs, tissue scaffolds, CSF shunts, dental fracture repair devices, intravitreal drug delivery devices, nerve regeneration conduits, electrostimulation leads, spinal/orthopedic repair devices, wound dressings, embolic protection filters, abdominal aortic aneurysm grafts and devices, neuroaneurysm treatment coils, hemodialysis devices, uterine bleeding patches, anastomotic closures, aneurysm exclusion devices, neuropatches, vena cava filters, urinary dilators, endoscopic surgical and wound drainings, bandages, surgical tissue extractors, transition sheaths and dialators, coronary and peripheral guidewires, circulatory support systems, tympanostomy vent tubes, cerebro-spinal fluid shunts, defibrillator leads, percutaneous closure devices, drainage tubes, bronchial tubes, vascular coils, vascular protection devices, vascular intervention devices including vascular filters and distal support devices and emboli filter/entrapment aids, AV access grafts, surgical tampons, and cardiac valves.

The following examples are included to demonstrate preferred embodiments of the invention. It should be appreciated by those of skill in the art that the techniques disclosed in the examples, which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

We previously identified chemical entities that elicited antivirulence activity against MRSA causing diminished production of the staphylococcal toxins, α-Hemolysin, also known as α-toxin (Hla) and Phenol-Soluble Modulin (PSM-a) in a dose-dependent manner. Virtual screening was employed to discover small molecules that block the phosphorylation site on the regulatory domain of AgrA, a response regulatory protein integral to the toxin biosynthetic pathway in MRSA. Initial results indicated that the small molecules inhibited the transcription of the Hla and PSM-α. One of the compounds discovered as an initial candidate, inhibited rabbit erythrocyte hemolysis by 98 and 9% at 10 and 1 g/mL, respectively. Based on the biaryl hydroxyketone structural scaffold of this candidate we applied chemical synthesis to derivatize the aromatic rings in order to discover compounds with more potent antivirulence activity.

In this example, we describe a concise synthesis of 148 individual chemical entities through a robust acylation method that affords a range of biarylhydroxyketones in high yields and in a single step. Furthermore, the in vitro efficacy of this library was evaluated by a rabbit blood hemolysis assay affording a subset of efficacious antivirulence agents. The underlying bond disconnection resulting in the generation of a library of derivatives is the acylation bond-forming process affording resorcinols (1) as the nucleophilic synthon and aryloxy acetonitriles (2) as the electrophilic synthon as shown in FIG. 2(A). This strategy led to the discovery of new compounds with considerably higher quorum sensing inhibitory activity than the parent compound.

The retrosynthetic analysis of biaryl hydroxyketone moiety, as shown in FIG. 2A allowed for resorcinol derivatives (represented by 1) and aryloxy acetonitriles (represented by 2) as convenient starting points for the assembly of the targeted library. FIG. 2A shows the individual variations selected based on availability of substituted resorcinols and aryloxyacetonitrile precursors. All of the resorcinol derivatives were commercially available except for 4-methyl and 4-propyl substitutions represented by 1d and 1e (necessary for synthesis of 4d and 4e series respectively). These were synthesized using reduction reactions of corresponding carbonyl compounds. All the substitutions of aryloxyacetonitrile compounds desired for the construction of targeted library needed to be synthesized. Alkylation reaction of phenols with α-bromoacetonitriles reported by McManus et al. served as a template for the synthesis of these precursors. Individual protocols were adapted based on existing methods to provide precursors in excellent yields.

As shown in FIG. 2B, a Lewis-acid catalyzed Friedel-Crafts' acylation step involving the activation of the nitrile functionality of 2 by $ZnCl_2$ followed by nucleophilic attack by 1 was executed in the presence of gaseous hydrogen chloride in benzene-diethyl ether mixture to yield the iminium hydrochlorides 3 as the intermediate. Upon hydrolysis of 3 the biaryl hydroxy ketone library (represented by 4) was obtained in moderate to excellent yields depending on individual substitution pattern. Each derivatization reaction afforded product 4 in moderate to high yields averaging about 70%. Purification of the compounds was relatively simple as a large number of products crystallized, thereby not requiring chromatography. Though a few of these biaryl hydroxyketones were reported in the literature, this is the first collective synthetic study documenting this class of compounds directly in a single operation. Structural characterization of each member of the library was performed through 1H, 13C NMR analyses. Analogs 4a-1 and 4a-11 yielded X-ray diffraction data. Table 1 lists the individual substitutions on each derivative that was synthesized using this one-step method.

TABLE 1

Percent Homolysis and Growth Assay of compounds 4a-4f

| | | | 10 µg/mL | | 1 µg/mL | |
|---|---|---|---|---|---|---|
| $R^1$ | $R^2$ | Compound | Growth | Hemolysis | Growth | Hemolysis |
| | | 4a1 to 4a29 | | | | |
| | | DMSO | 100 | 100 ± 2.4 | 100 | 100.0 ± 10.0 |
| | | Diflunisal | 100.1 | 2.3 ± 0.1 | 102.1 | 37.0 ± 1.1 |
| 5-H | H | 4a-0 | 109.7 | 31.5 ± 0.9 | | |
| 5-H | m-F | 4a-1 | 99.4 | 10.1 ± 0.5 | 98.7 | 81.0 ± 4.4 |
| 5-H | o-Cl | 4a-2 | 105.7 | 7.6 ± 0.4 | 104.6 | 99.7 ± 2.1 |
| 5-H | m-Cl | 4a-3 | 79.5 | 1.2 ± 0.2 | 106.8 | 83.2 ± 4.7 |
| 5-H | p-Cl | 4a-4 | 95.5 | 7.5 ± 0.5 | 96.7 | 119.1 ± 7.4 |
| 5-H | o-F | 4a-5 | 101.8 | 26.7 ± 1.5 | | |
| 5-H | p-F | 4a-6 | 105.5 | 39.7 ± 3.8 | | |
| 5-H | p-Br | 4a-7 | 68.9 | 5.7 ± 1.1 | 98.7 | 97.0 ± 3.9 |
| 5-H | p-I | 4a-8 | 69.6 | 1.4 ± 0.0 | 94.2 | 74.8 ± 9.9 |
| 5-H | o-Me | 4a-9 | 89.8 | 14.0 ± 0.6 | 103.6 | 113.3 ± 4.4 |

TABLE 1-continued

Percent Homolysis and Growth Assay of compounds 4a-4f

| | | | 10 µg/mL | | 1 µg/mL | |
|---|---|---|---|---|---|---|
| R¹ | R² | Compound | Growth | Hemolysis | Growth | Hemolysis |
| 5-H | m-Me | 4a-10 | 100.2 | 90.5 ± 6.2 | | |
| 5-H | p-Me | 4a-11 | 38.7 | 4.2 ± 10.4 | | |
| 5-H | 2,4-$F_2$ | 4a-12 | 98.8 | 17.2 ± 2.4 | 100.7 | 107.9 ± 8.1 |
| 5-H | 2,6-$F_2$ | 4a-13 | 105.8 | 65.4 ± 2.4 | | |
| 5-H | 3,4-$F_2$ | 4a-14 | 106.5 | 46.5 ± 2.7 | | |
| 5-H | 3,5-$F_2$ | 4a-15 | 95.8 | 7.8 ± 2.5 | 97.5 | 77.0 ± 2.4 |
| 5-H | 2,4,5-$F_3$ | 4a-16 | 110.5 | 45.1 ± 1.6 | | |
| 5-H | 3,4,5-$F_3$ | 4a-17 | 103.6 | 9.1 ± 0.1 | | |
| 5-H | Pentafluoro | 4a-18 | 99.1 | 19.6 ± 4.1 | 105.2 | 133.7 ± 6.9 |
| 5-H | p-iPr | 4a-19 | 8.3 | −2.3 ± 0.0 | 104.3 | 80.4 ± 10.1 |
| 5-H | p-tBu | 4a-20 | 4.3 | −3.3 ± 0.1 | 108 | 79.7 ± 1.8 |
| 5-H | p-Ph | 4a-21 | 100.4 | 29.4 ± 2.9 | | |
| 5-H | p-$NO_2$ | 4a-22 | 106.5 | 47.6 ± 0.8 | | |
| 5-H | o-COOH | 4a-23 | 100.8 | 107.6 ± 1.8 | | |
| 5-H | m-COOH | 4a-24 | 101.9 | 80.5 ± 6.5 | | |
| 5-H | p-$OCH_3$ | 4a-26 | 104.3 | 48.2 ± 2.6 | | |
| 5-H | o-$COOCH_3$ | 4a-27 | 102 | 58.9 ± 5.1 | | |
| 5-H | m-$COOCH_3$ | 4a-28 | 100.1 | 24.2 ± 2.0 | | |
| 5-H | p-$COOCH_3$ | 4a-29 | 100.3 | 29.7 ± 0.6 | | |
| | | 4b1 to 4b29 | | | | |
| | | DMSO | 100 | 100 ± 2.4 | 100 | 100.0 ± 10.0 |
| | | PC | 100.6 | 2.1 ± 0.0 | 102.4 | 90.8 ± 6.6 |
| 5-Ethyl | H | 4b-0 | 100.6 | 2.1 ± 0.2 | 102.4 | 90.8 ± 6.6 |
| 5-Ethyl | m-F | 4b-1 | 97.7 | 22.4 ± 3.9 | 93.5 | 88.5 ± 12.8 |
| 5-Ethyl | o-Cl | 4b-2 | 78.9 | 0.9 ± 0.0 | 102.4 | 80.6 ± 0.4 |
| 5-Ethyl | m-Cl | 4b-3 | 32.4 | −0.2 ± 0.0 | 103.3 | 102.7 ± 11.3 |
| 5-Ethyl | p-Cl | 4b-4 | 32.4 | 0.3 ± 0.0 | 101.4 | 145.9 ± 33.9 |
| 5-Ethyl | o-F | 4b-5 | 105.2 | 9.3 ± 0.1 | 104.9 | 85.5 ± 10.4 |
| 5-Ethyl | p-F | 4b-6 | 100.2 | 11.1 ± 0.2 | 102.3 | 85.1 ± 7.0 |
| 5-Ethyl | p-Br | 4b-7 | 10.5 | −0.1 ± 0.0 | 104 | 159.4 ± 27.3 |
| 5-Ethyl | p-I | 4b-8 | 17.7 | −0.3 ± 0.0 | 102 | 110.7 ± 10.0 |
| 5-Ethyl | o-Me | 4b-9 | 51.4 | 0.4 ± 0.0 | 103.7 | 72.9 ± 5.5 |
| 5-Ethyl | m-Me | 4b-10 | 86 | 1.6 ± 0.1 | 102 | 66.7 ± 3.4 |
| 5-Ethyl | p-Me | 4b-11 | 78.1 | 0.1 ± 0.0 | 103.3 | 50.3 ± 2.9 |
| 5-Ethyl | 2,4-$F_2$ | 4b-12 | 93.2 | 1.7 ± 0.2 | 104.7 | 52.3 ± 2.1 |
| 5-Ethyl | 2,6-$F_2$ | 4b-13 | 85.1 | 1.2 ± 0.1 | 105 | 48.1 ± 3.5 |
| 5-Ethyl | 3,4-$F_2$ | 4b-14 | 79.2 | 0.0 ± 0.0 | 106.7 | 53.6 ± 3.8 |
| 5-Ethyl | 3,5-$F_2$ | 4b-15 | 63.9 | −0.4 ± 0.0 | 107.4 | 49.3 ± 3.7 |
| 5-Ethyl | 2,4,5-$F_3$ | 4b-16 | 81.3 | 1.1 ± 0.1 | 105 | 66.1 ± 7.4 |
| 5-Ethyl | 3,4,5-$F_3$ | 4b-17 | 40.8 | 0.6 ± 0.1 | 102.8 | 98.5 ± 4.0 |
| 5-Ethyl | Pentafluoro | 4b-18 | 4.1 | 0.7 ± 0.0 | 97.2 | 117.4 ± 6.4 |
| 5-Ethyl | p-iPr | 4b-19 | 2.1 | −1.3 ± 0.2 | 95.4 | 55.5 ± 9.8 |
| 5-Ethyl | p-tBu | 4b-20 | 1 | 0.4 ± 0.0 | 93.6 | 50.6 ± 1.7 |
| 5-Ethyl | p-Ph | 4b-21 | 30.4 | −0.4 ± 0.0 | 100.9 | 81.6 ± 14.1 |
| 5-Ethyl | p-$NO_2$ | 4b-22 | 103.1 | 144.6 ± 6.9 | | |
| 5-Ethyl | o-COOH | 4b-23 | 101.4 | 107.8 ± 3.3 | | |
| 5-Ethyl | m-COOH | 4b-24 | 106.3 | 70.3 ± 3.4 | | |
| 5-Ethyl | p-OCH3 | 4b-26 | 98.1 | 12.6 ± 0.7 | 102.9 | 167.4 ± 19.3 |
| 5-Ethyl | o-$COOCH_3$ | 4b-27 | 97.8 | 29.3 ± 2.1 | | |
| 5-Ethyl | m-$COOCH_3$ | 4b-28 | 94.2 | 8.8 ± 0.5 | 100.1 | 78.4 ± 5.5 |
| 5-Ethyl | p-$COOCH_3$ | 4b-29 | 90.2 | 4.5 ± 0.3 | 106.1 | 144.8 ± 20.6 |
| | | 4c-1 to 4c-29 | | | | |
| | | DMSO | 100 | 100 ± 2.4 | 100 | 100 ± 10.0 |
| 6-OH | H | 4c-0 | 108.2 | 46.3 ± 1.9 | | |
| 6-OH | m-F | 4c-1 | 76.9 | 1.4 ± 0.1 | 105.4 | 119.9 ± 18.5 |
| 6-OH | o-Cl | 4c-2 | 70.1 | 1.8 ± 0.3 | 106.7 | 100.7 ± 17.0 |
| 6-OH | m-Cl | 4c-3 | 17.8 | 0.1 ± 0.0 | 102.9 | 152.6 ± 14.0 |
| 6-OH | p-Cl | 4c-4 | 82.6 | 33.0 ± 2.9 | | |
| 6-OH | o-F | 4c-5 | 100 | 23.3 ± 1.5 | | |
| 6-OH | p-F | 4c-6 | 106 | 43.3 ± 2.7 | | |
| 6-OH | p-Br | 4c-7 | 75.1 | 8.3 ± 0.3 | 99.6 | 114.6 ± 19.1 |
| 6-OH | p-I | 4c-8 | 45 | 0.1 ± 0.0 | 101.9 | 146.9 ± 6.7 |
| 6-OH | o-Me | 4c-9 | 85.3 | 5.4 ± 0.1 | 109.1 | 103.5 ± 3.2 |
| 6-OH | m-Me | 4c-10 | 107.5 | 4.9 ± 0.5 | 106.5 | 106.0 ± 3.2 |
| 6-OH | p-Me | 4c-11 | 108.5 | 10.8 ± 1.4 | 110.8 | 99.9 ± 14.1 |
| 6-OH | 2,4-$F_2$ | 4c-12 | 119.3 | 44.0 ± 1.7 | | |
| 6-OH | 2,6-$F_2$ | 4c-13 | 114.7 | 23.0 ± 3.1 | | |
| 6-OH | 3,4-$F_2$ | 4c-14 | 112.7 | 37.8 ± 2.8 | | |
| 6-OH | 3,5-$F_2$ | 4c-15 | 94.7 | 9.2 ± 0.9 | 114.6 | 95.8 ± 4.8 |
| 6-OH | 2,4,5-$F_3$ | 4c-16 | 111 | 21.7 ± 2.3 | | |
| 6-OH | 3,4,5-$F_3$ | 4c-17 | 34.6 | 1.2 ± 0.0 | 100.8 | 128.8 ± 17.6 |
| 6-OH | Pentafluoro | 4c-18 | 55.9 | 4.2 ± 0.4 | 105.5 | 115.2 ± 28.1 |

TABLE 1-continued

Percent Homolysis and Growth Assay of compounds 4a-4f

| | | | 10 μg/mL | | 1 μg/mL | |
|---|---|---|---|---|---|---|
| R¹ | R² | Compound | Growth | Hemolysis | Growth | Hemolysis |
| 6-OH | p-iPr | 4c-19 | 95.9 | 7.1 ± 0.3 | 110.6 | 127.0 ± 13.6 |
| 6-OH | p-tBu | 4c-20 | 2 | 0.7 ± 0.0 | 100.7 | 87.0 ± 0.5 |
| 6-OH | p-Ph | 4c-21 | 1.9 | 3.0 ± 0.1 | 102.7 | 114.5 ± 16.9 |
| 6-OH | p-NO₂ | 4c-22 | 88.7 | 81.1 ± 2.7 | | |
| 6-OH | p-COOH | 4c-25 | | | | |
| 6-OH | p-OCH₃ | 4c-26 | 106.5 | 70.5 ± 7.1 | | |
| 6-OH | o-COOCH₃ | 4c-27 | 103.8 | 90.0 ± 1.0 | | |
| 6-OH | m-COOCH₃ | 4c-28 | 102.8 | 90.5 ± 5.9 | | |
| 6-OH | p-COOCH₃ | 4c-29 | 98.2 | 103.3 ± 1.1 | | |
| | | 4d-1 to 4d-29 | | | | |
| | | DMSO | 100 | 100 ± 2.4 | 100 | 100.0 ± 10.0 |
| 5-Methyl | H | 4d-0 | 100 | 68.4 ± 13.0 | | |
| 5-Methyl | m-F | 4d-1 | 103 | 53.0 ± 13.2 | | |
| 5-Methyl | o-Cl | 4d-2 | 104.6 | 19.1 ± 1.3 | 102.4 | 107.9 ± 5.6 |
| 5-Methyl | m-Cl | 4d-3 | 103.4 | 8.4 ± 1.4 | 102.1 | 204.2 ± 45.4 |
| 5-Methyl | p-Cl | 4d-4 | 103.8 | 12.9 ± 2.8 | 99.5 | 169.3 ± 23.8 |
| 5-Methyl | o-F | 4d-5 | 103.6 | 34.1 ± 3.6 | | |
| 5-Methyl | p-F | 4d-6 | 104.2 | 33.6 ± 10.2 | | |
| 5-Methyl | p-Br | 4d-7 | 103.4 | 29.5 ± 2.9 | | |
| 5-Methyl | p-I | 4d-8 | 98.6 | 8.7 ± 1.2 | 102.4 | 195.4 ± 32.2 |
| 5-Methyl | o-Me | 4d-9 | 102 | 43.0 ± 8.4 | | |
| 5-Methyl | m-Me | 4d-10 | 100.8 | 29.3 ± 10.7 | | |
| 5-Methyl | p-Me | 4d-11 | 84.2 | 14.3 ± 2.8 | 102.9 | 248.4 ± 41.9 |
| 5-Methyl | 2,4-F₂ | 4d-12 | 105.7 | 3.8 ± 0.6 | 94.8 | 149.5 ± 21.6 |
| 5-Methyl | 2,6-F₂ | 4d-13 | 97.6 | 34.3 ± 1.8 | | |
| 5-Methyl | 3,4-F₂ | 4d-14 | 108.7 | 3.1 ± 0.3 | 106 | 221.3 ± 20.5 |
| 5-Methyl | 3,5-F₂ | 4d-15 | 102 | 12.5 ± 3.2 | 101.3 | 149.3 ± 19.2 |
| 5-Methyl | 2,4,5-F₃ | 4d-16 | 100.5 | 28.3 ± 6.6 | | |
| 5-Methyl | 3,4,5-F₃ | 4d-17 | 95.9 | 7.0 ± 1.1 | 99.6 | 170.5 ± 9.9 |
| 5-Methyl | Pentafluoro | 4d-18 | 82.8 | 5.1 ± 1.0 | 104.4 | 180.1 ± 14.4 |
| 5-Methyl | p-iPr | 4d-19 | 5.2 | 1.0 ± 0.1 | 99.5 | 29.0 ± 0.5 |
| 5-Methyl | p-tBu | 4d-20 | 0.9 | −0.6 ± 0.1 | 104 | 22.9 ± 0.5 |
| 5-Methyl | p-Ph | 4d-21 | 3.2 | 5.7 ± 1.3 | 107.7 | 52.1 ± 10.8 |
| 5-Methyl | p-NO₂ | 4d-22 | 101.7 | 98.8 ± 11.0 | | |
| 5-Methyl | p-COOH | 4d-25 | 105.2 | 124.8 ± 1.3 | | |
| 5-Methyl | p-OCH₃ | 4d-26 | 94.9 | 52.0 ± 7.8 | | |
| 5-Methyl | o-COOCH₃ | 4d-27 | 101 | 35.9 ± 0.6 | | |
| 5-Methyl | m-COOCH₃ | 4d-28 | 96.7 | 14.6 ± 1.0 | | |
| 5-Methyl | p-COOCH₃ | 4d-29 | 82.4 | 31.5 ± 3.1 | | |
| | | 4e-0 to 4e-29 | | | | |
| | | DMSO | 100 | 100 ± 2.4 | 100 | 100.0 ± 10.0 |
| 5-Propyl | H | 4e-0 | 85.6 | 4.3 ± 0.1 | 100.7 | 50.3 ± 3.2 |
| 5-Propyl | m-F | 4e-1 | 55.2 | 1.6 ± 0.2 | 104.3 | 36.9 ± 1.1 |
| 5-Propyl | o-Cl | 4e-2 | 3.2 | 1.3 ± 0.1 | 101.5 | 20.3 ± 1.9 |
| 5-Propyl | p-Cl | 4e-4 | 4.9 | −0.3 ± 0.0 | 104.3 | 30.9 ± 0.5 |
| 5-Propyl | o-F | 4e-5 | 63.9 | 0.4 ± 0.0 | 101.1 | 36.4 ± 1.9 |
| 5-Propyl | p-F | 4e-6 | 78.3 | 1.1 ± 0.1 | 101.4 | 34.2 ± 3.2 |
| 5-Propyl | p-Br | 4e-7 | 97.8 | 74.3 ± 13.7 | | |
| 5-Propyl | p-I | 4e-8 | 89.9 | 16.7 ± 0.5 | 99.5 | 27.6 ± 2.7 |
| 5-Propyl | o-Me | 4e-9 | 2.2 | −0.4 ± 0.0 | 100.4 | 20.3 ± 3.0 |
| 5-Propyl | m-Me | 4e-10 | 88.4 | 11.5 ± 1.2 | 98.9 | 18.7 ± 0.7 |
| 5-Propyl | p-Me | 4e-11 | 96.2 | 30.3 ± 4.2 | | |
| 5-Propyl | 2,4-F₂ | 4e-12 | 54.2 | 1.1 ± 0.1 | 100.4 | 14.4 ± 0.4 |
| 5-Propyl | 2,6-F₂ | 4e-13 | 38 | 1.3 ± 0.1 | 105.9 | 27.3 ± 1.9 |
| 5-Propyl | 3,4-F₂ | 4e-14 | 64.9 | −3.0 ± 0.1 | 107.2 | 9.6 ± 2.2 |
| 5-Propyl | 3,5-F₂ | 4e-15 | 80 | −1.8 ± 0.1 | 102.7 | 11.9 ± 0.5 |
| 5-Propyl | 3,4,5-F₃ | 4e-17 | 77.5 | −2.4 ± 0.3 | 104.7 | 14.8 ± 0.4 |
| 5-Propyl | Pentafluoro | 4e-18 | 1.3 | −2.9 ± 0.4 | 97.5 | 41.9 ± 0.4 |
| 5-Propyl | p-iPr | 4e-19 | 6 | −2.1 ± 0.1 | 95.6 | 22.9 ± 0.4 |
| 5-Propyl | p-tBu | 4e-20 | 2.6 | −1.6 ± 0.1 | 89.1 | 7.1 ± 0.1 |
| 5-Propyl | p-Ph | 4e-21 | 5.2 | 0.2 ± 0.0 | 83.5 | 24.2 ± 0.5 |
| 5-Propyl | p-NO₂ | 4e-22 | 103.1 | 45.3 ± 4.8 | | |
| 5-Propyl | p-COOH | 4e-25 | 102.1 | 8.3 ± 0.5 | 102.8 | 66.1 ± 4.7 |
| 5-Propyl | p-OCH₃ | 4e-26 | 91.2 | 2.4 ± 0.5 | 101.1 | 84.2 ± 8.0 |
| 5-Propyl | o-COOCH₃ | 4e-27 | 104.8 | 25.2 ± 3.0 | | |
| 5-Propyl | m-COOCH₃ | 4e-28 | 94.9 | 20.9 ± 0.9 | | |
| 5-Propyl | p-COOCH₃ | 4e-29 | 95.9 | 3.1 ± 0.1 | 103.9 | 109.2 ± 17.3 |
| | | 4f-1 to 4f-29 | | | | |
| | | DMSO | 100 | 100 ± 2.4 | 100 | 100.0 ± 10.0 |
| 5-Hexyl | H | 4f-0 | 103.5 | 6.6 ± 0.3 | 102.2 | 46.1 ± 2.2 |
| 5-Hexyl | m-F | 4f-1 | 106 | 9.3 ± 1.11 | 103.7 | 95.4 ± 1.2 |

TABLE 1-continued

Percent Homolysis and Growth Assay of compounds 4a-4f

| | | | 10 µg/mL | | 1 µg/mL | |
|---|---|---|---|---|---|---|
| R¹ | R² | Compound | Growth | Hemolysis | Growth | Hemolysis |
| 5-Hexyl | o-Cl | 4f-2 | | | | |
| 5-Hexyl | p-Cl | 4f-4 | | | | |
| 5-Hexyl | o-F | 4f-5 | | | | |
| 5-Hexyl | p-F | 4f-6 | | | | |
| 5-Hexyl | p-Br | 4f-7 | | | | |
| 5-Hexyl | p-I | 4f-8 | 100.2 | 25.3 ± 1.9 | | |
| 5-Hexyl | o-Me | 4f-9 | | | | |
| 5-Hexyl | m-Me | 4f-10 | | | | |
| 5-Hexyl | p-Me | 4f-11 | | | | |
| 5-Hexyl | 2,4-F$_2$ | 4f-12 | 15.4 | −2.5 ± 0.1 | 73.3 | 1.9 ± 0.1 |
| 5-Hexyl | 2,6-F$_2$ | 4f-13 | | | | |
| 5-Hexyl | 3,4-F$_2$ | 4f-14 | 104.1 | 11.8 ± 1.3 | 100.3 | 15.2 ± 1.2 |
| 5-Hexyl | 3,5-F$_2$ | 4f-15 | | | | |
| 5-Hexyl | 3,4,5-F$_3$ | 4f-17 | | | | |
| 5-Hexyl | Pentafluoro | 4f-18 | | | | |
| 5-Hexyl | p-iPr | 4f-19 | 92.7 | 62.0 ± 14.5 | | |
| 5-Hexyl | p-tBu | 4f-20 | 109.2 | 0.2 ± 0.0 | 97.3 | 175.8 ± 12.2 |
| 5-Hexyl | p-Ph | 4f-21 | 98.7 | 11.0 ± 1.4 | 101.7 | 34.5 ± 0.7 |
| 5-Hexyl | p-NO$_2$ | 4f-22 | 105.9 | 28.0 ± 2.4 | | |
| 5-Hexyl | p-COOH | 4f-25 | | | | |
| 5-Hexyl | p-OCH$_3$ | 4f-26 | 55.9 | 16.1 ± 1.0 | 94.5 | 24.3 ± 1.8 |
| 5-Hexyl | o-COOCH$_3$ | 4f-27 | 92.7 | 7.2 ± 0.7 | 99.3 | 72.6 ± 7.0 |
| 5-Hexyl | m-COOCH$_3$ | 4f-28 | 83.4 | 4.5 ± 0.3 | 100.3 | 10.2 ± 1.1 |
| 5-Hexyl | p-COOCH$_3$ | 4f-29 | 99.7 | 1.9 ± 0.1 | 98.6 | 9.5 ± 0.5 |

Efficacy of the Biarylhydroxyketone Library Against MRSA-Triggered Hemolysis

Figure 3:
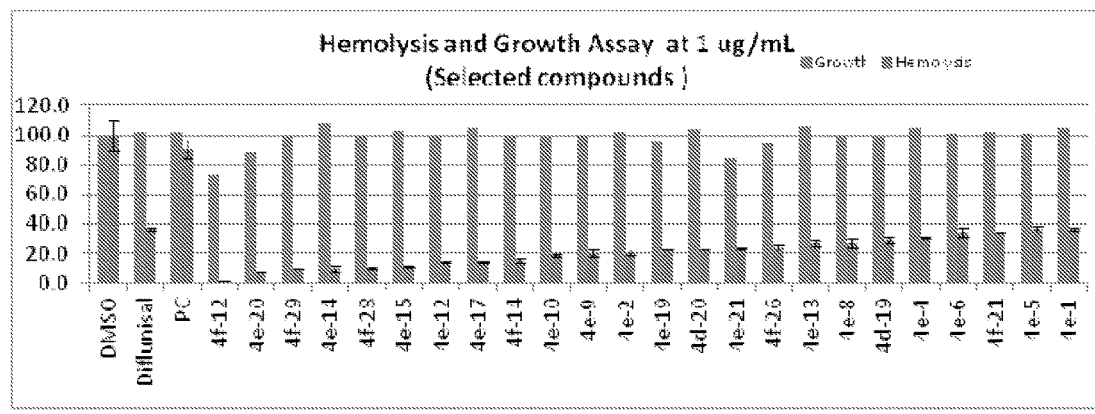
FIG. 3 is a graph that shows hemolysis and growth at 1 μ/ml.

The antivirulence activity of these compounds against MRSA strain USA 300 was measured by the extent of hemolysis inhibition in rabbit erythrocytes in vitro. MRSA secretes the cytotoxin Hla, which creates holes in red blood cells of rabbits and other organisms (causing hemolysis). The assay measures the level of hemoglobin released from the erythrocytes through this rupture. In addition to hemolysis, we measured the extent to which the family of biaryl hydroxyketones 4 inhibited bacterial growth. For antivirulence candidates, it was anticipated to observe a high magnitude of hemolysis inhibition (indicated by a lower % for hemolysis) concomitantly with no or low inhibition of bacterial growth. Molecules conferring such effect are desirable because they are good candidates for eliminating virulence and low potential for resistance development. The hemolysis data for all 148 compounds is shown as grouped sections in Table 1 along with data on bacterial growth inhibition. Through screening this relatively large library for efficacy, we identified a subset of 24 analogs displaying the most efficacious hemolysis inhibition at a concentration of 1 µg/mL. These results are plotted in FIG. 3. DMSO was used as a control, assigned 100% hemolysis and 100% series. This trend points to the beneficial effect of having sterically larger substitutions on the resorcinol portion. In the presence of 1 µg/mL of the most efficacious compound, 4f-12, rabbit erythrocyte hemolysis was only 1.9±0.1% compared 100% in the absence of the compound. However, this compound inhibited bacterial growth by 26.7% at a concentration of 1 µg/mL, as shown in Table 1. Thus, some decrease in hemolysis can be attributed to a lesser amount of bacteria present. However, 4f-12 has been shown to inhibit binding of AgrA to its cognate DNA by an electrophoretic mobility shift assay (data not shown), thereby inhibiting the production of the α-toxin, the agent causing hemolysis. Thus, 4f-12 has dual activity. It is a bacteriostatic agent in addition to being an antivirulence compound.

The presence of a larger hexyl side chain on the 5-position of resorcinol ring of 4f-12 in addition to the presence of two fluorine atoms on the aryloxy portion of this molecules are noteworthy and seem to confer a significant levels of hemolysis inhibitory effect. This trend is seen to be operative across the rest of the 23 derivatives mapped in FIG. 3 revealing the effects of hydrophobic groups present on either one or both aromatic rings. The exact nature of substitution seems only moderately specific for rendering hemolysis inhibitory activity. For example, the fluorine atoms could be replaced by methyl groups or isopropyl groups and the activity is maintained albeit with minor differences.

Few naturally occurring compounds contain fluorine atoms but introduction of fluorines has become an important tool in modern drug discovery. Fluorine has some physical properties that are considered beneficial for drug development. It is more lipophilic than hydrogen, thus increasing the affinity to hydrophobic binding sites. Its high electronegativity enables it to serve as a hydrogen acceptor, an added functionality for binding to proteins. Furthermore, a more lipophilic substance will partition more readily into membranes, thus increasing its bioavailability. Therefore, it is not surprising that many drugs on the market today contain at least one fluorine substituent. For example, Lipitor (atorvastatin) has one aromatic fluorine atom. The popular antidepressant Prozac (fluoxetine) contains a para-phenyl trifluoromethyl group. The non-steroidal anti-inflammatory drug Diflunisal contains two aromatic fluorine atoms. Interestingly, Diflunisal was discovered in our preliminary screening to have antivirulence activity against MRSA, demonstrating a new use for an old drug.

Toxins secreted by S. aureus cause damage to host cells and impair the ability of host defense mechanisms to fight the infection. Blocking toxin expression should therefore enable the immune system to contain the infection. The most important S. aureus operon for the expression of toxins is the agr system, which is activated by a quorum sensing mechanism. The autoinducing peptide serves as the signaling molecule to activate the histidine kinase AgrC, which in turn activates the response regulator AgrA to bind to its cognate DNA to drive the expression of a series of toxins and virulence factors. Several accounts of agr inhibition have been reported. AgrC was the target in a synthetic approach to inhibit agr activation by cyclic peptide mimics of the autoinducing peptide (AIP). Sequestration of the autoinducing peptide by designed inhibitory antibodies was another approach to quench agr expression. Depsipeptides isolated from a marine bacterium and ambuic acid isolated from a fungus have been shown to inhibit expression of the agr system, apparently by competition with the AIPs.

Methods

All commercially available reagents and solvent were used as analytically pure substances as received. Reactions were monitored by thin-layer chromatography (TLC) on silica gel plates (60 F254) with a fluorescent indicator, and independently visualized with UV light. Target molecules 4a-4f were recrystallized from 2-propanol. Yields refer to crystallized compounds. Target molecules 4a-4f were recrystallized from 2-propanol. All separations of intermediates (1d, 1e, 2a-2aa) were carried out under flash chromatography (Silica gel grade: 200-400 mesh, 40-63 μm) at medium pressure (20 psi). All new compounds gave satisfactory spectroscopic analyses (1H NMR, 13C NMR). NMR spectra were recorded at 400 MHz in CDCl3 or Acetone-d6 and chemical shift values ($\delta$) are given in ppm. 1H NMR spectra are reported in parts per million ($\delta$) relative to the residual (indicated) solvent peak. Data for 1H NMR are reported as follows: chemical shift ($\delta$ ppm), multiplicity (s=singlet, bs=broad singlet, d=doublet, t=triplet, q=quartet, ddd=double double doublet, m=multiplet, cm=complex multiplet), integration, and coupling constants in Hz. 13C NMR spectra were obtained on 400 MHz spectrometers (100 MHz actual frequency) and are reported in parts per million ($\delta$) relative to the residual (indicated) solvent peak. $^{19}$F NMR spectra were obtained on 400 MHz spectrometers (376 MHz actual frequency) and are reported in parts per million ($\delta$). High-resolution mass spectrometry (HRMS) data were obtained on spectrometer with a quadrupole analyzer. All melting points for solids are reported uncorrected.

General Procedure for synthesis of α-aryloxy-2,4-dihydroxy-substitued acetophenones 4a-4f Dry hydrogen chloride was passed for 1 h into a solution of 2 (1 mmol, 1.0 equiv.) in dry benzene (1.5 mL) at 0° C. A solution of the substituted-resorcinol 1 (1.2 mmol, 1.2 equiv.) and ZnCl2 (0.136 g, 1 mmol, 1.0 equiv.) in 1.5 mL dry ether were then added. Dry hydrogen chloride was bubbled for an additional 2 h and the reaction mixture was left overnight. The liquid was decanted from the solid, hot water (8 mL) was added to the residue, and the mixture was boiled at 80-100° C. for 2-3 h. After cooling, the solid that formed was filtered off, washed with water until pH reached 7, and recrystallized from 2-propanol to yield 4.

Substituted resorcinols 1a, 4-ethylresorcinol 1b, benzene-1,3,5-triol 1c and 4-hexylresorcinol 1f are commercial available. 4-methylresorcinol 1d and 4-propylresorcinol 1e was prepared according to the methods outlined by Hobbs et al. and Mizobuchi et al. The NMR spectra for 1d and 1e matched those reported in the literature.

4-methylresorcinol 1d 2,4-Dihydroxybenaldehyde was reduced by hydrogen with Palladium on Carbon as catalyst to give 1d. Yield 87.4%, m.p. 104° C. (lit. 106° C. (1)). $^1$H NMR (400 MHz, Acetone-d$_6$) $\delta$ 7.92 (d, J=35.8 Hz, 2H), 6.84 (d, J=8.1 Hz, 1H), 6.35 (d, J=2.3 Hz, 1H), 6.22 (dd, J=8.1, 2.4 Hz, 1H), 2.06 (s, 3H).

4-propylresorcinol 1e 1-(2,4-dihydroxyphenyl)propan-1-one was reduced by zinc amalgam in ethanol and water mixture solvent to give 1e. Yield 83.6%, m.p. 80-81° C. (lit. 82° C. (2)). $^1$H NMR (400 MHz, Acetone-d$_6$) $\delta$ 7.92 (d, J=23.5 Hz, 2H), 6.84 (d, J=8.1 Hz, 1H), 6.35 (d, J=2.2 Hz, 1H), 6.24 (dd, J=8.1, 2.4 Hz, 1H), 2.52-2.41 (m, 2H), 1.65-1.42 (m, 2H), 0.89 (t, J=7.4 Hz, 3H).

The aryloxyacetonitrile precursors 2 were prepared according to a literature procedure reported by McManus et al. To a solution of bromoacetonitrile 1.42 g (12 mmol, 1.2 equiv.) and 10 mmol (1.0 equiv.) substituted-phenol in acetone (10 mL) was added K$_2$CO$_3$ (2.76 g, 20 mmol, 2.0 equiv.) and the mixture was stirred for ~10-15 hours at room temperature. The mixture was filtered to provide the product as a precipitate. The residue was purified by flash chromatography (silica gel), eluting with ethyl acetate:hexanes (isocratic) (V:V=1:2) to provide of the desired product 2 in purified form. Table 1 lists the analytical data for compounds in this series.

Growth and Hemolysis Assay

All reagents and culture media were purchased from Fisher Scientific except rabbit blood (HemoStat Lab., Dixon, Calif., USA) and MRSA strain USA300, which was obtained from Dr. Robert Bonomo at the Louis Stokes Cleveland VA Medical Center. OD600 readings were recorded on a BioPhotometer; OD541 readings were recorded on a UV-1700 Pharmaspec instrument. MRSA strain USA300 was cultured overnight at 37° C. in 1.5 mL Tryptic Soy (TS) broth. The overnight culture was diluted 1 to 100 and 2 mL was added to designated incubation tubes. DMSO solutions of compound 4 were subsequently added to yield a final concentration of either 1 or 10 μg/mL compound in 2% DMSO. 100% DMSO was added to a control incubation tube. The tubes were placed in a shaker and incubated at 37° C. for 6 h. OD600 was measured every hour to generate a growth curve. After 6 h the bacterial samples were filtered through a 0.22 μm syringe filter (Fisher Scientific). 100 μL of the bacterial filtrate was added to 1 mL hemolysin buffer (0.145 M NaCl, 0.02 M CaCl2). 25 μL of defibrinated rabbit blood was added and incubated for 15 min at 37° C. The unlysed blood cells were pelleted by centrifugation (5,500×g, room temperature, 2 min) The hemolytic activity of the supernatant was determined by measuring the optical density of hemoglobin at 541 nm Defibrinated rabbit blood without bacterial filtrate served as blank (Db), 2% DMSO supernatant without anti-virulence agent served as control culture (Dc). The percent hemolysis was calculated by the formula H=(Dt−Db)/(Dc−Db)*100, where the Dt is the OD541 reading for supernatant with anti-virulence compound.

EXAMPLE 2

Virtual screening was carried out with a small-molecule library against the phosphoryl-binding pocket of the agr response regulator AgrA. Several compounds were discovered that inhibit the production of staphylococcal toxins, such as α-hemolysin (Hla) and phenol-soluble modulin α (PMS-α) in a dose-dependent matter. More potent compounds were discovered by structure-activity studies at online catalogs of chemical vendors and eventually by chemical synthesis of a combinatorial library of 148 compounds based on the most potent compound in the in vitro assay of hemolysis inhibition in rabbit erythrocytes (manuscript submitted). The most efficacious compound, codenamed F12 (4f12 identified above), inhibits rabbit erythrocyte hemolysis by 98% at the low concentration of 1 μg/ml.

Figure 4:
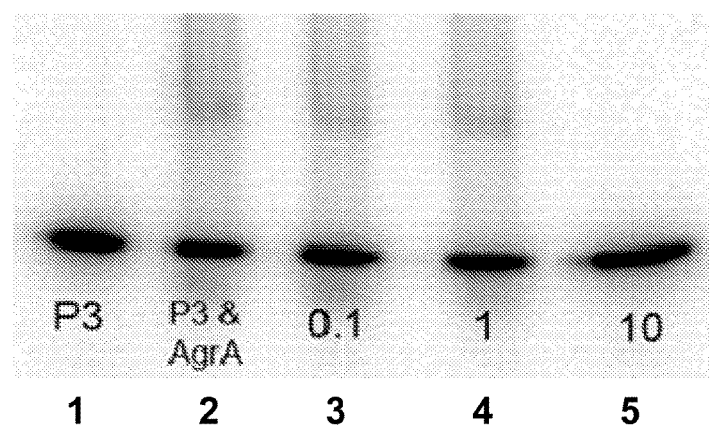
FIG. 4 illustrates electrophoretic mobility shift assay.

The most efficacious compounds F1 (4f1) and F12 (4f12) inhibit the formation of the AgrA-promoter P3 complex, as shown in FIG 4.

FIG. 4 is an electrophoretic mobility shift assay showing compound F12 inhibits the formation of the specific AgrA-DNA complex required for toxin formation. The leftmost lane contains 1 nM of a DNA oligonucleotide corresponding in sequence to the P3 promoter. In lane two 2 μM of purified recombinant AgrA was added. The higher molecular weight band in lane 2 corresponds to the AgrA-P3 complex. In the next lanes compound F12 was added at increasing concentrations of 0.1, 1 and 10 μM. The band of the AgrA-P3 complex disappears upon the addition of 10 μM F12, indicating that this compound inhibits the formation of the specific AgrA-DNA complex required for toxin formation. Similar results were obtained with compounds F1 and F19 (4f19).

Figure 5:
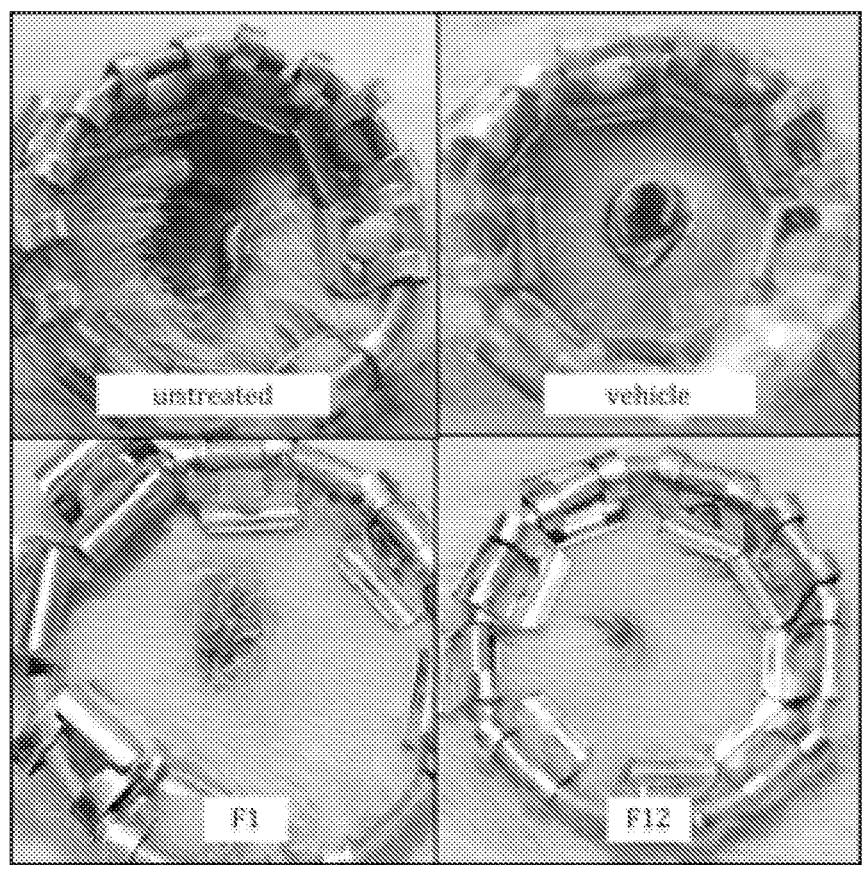
FIG. 5 illustrates and image showing MRSA mouse wound infection model.

FIG. 5 illustrates images showing compounds F1 and F12 improved wound healing, compared to untreated control, without having any effect on bacterial growth. Wounds were created in mice and inoculated with $10^7$ cfu of MRSA strain USA300. An hour later compounds F1 or F12 were added to the wounds at a dose of 20 mg/kg. This dose was repeated once a day for seven days. On day eight the animals were sacrificed and the area of the wound measured. Compounds F1 and F12 improved wound healing by 46.6 and 79.4%, respectively, compared to untreated control. However, there was no significant difference in the bacterial burden, indicating that the compounds have no effect on bacterial growth.

Figure 6:
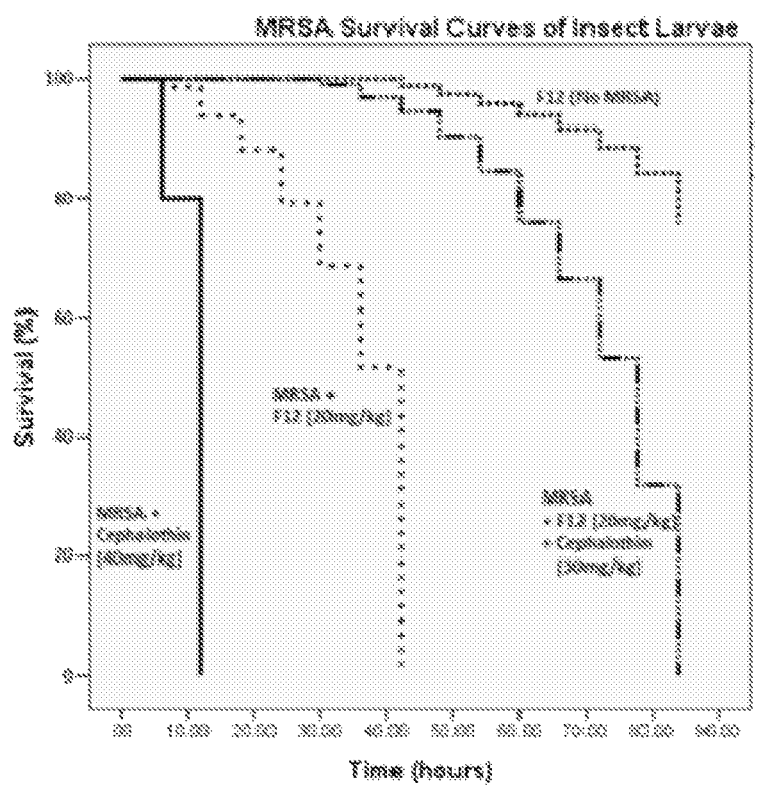
FIG. 6 illustrates MRSA Survival curves of insect larvae (*Galleria Mellonella*) in the presence compound F12 and cephalothin.

FIG. 6 is a graph illustrating the survival results of caterpillars injected with $2\times10^7$ cfu of MRSA strain USA300. Treatment was repeated every 6 hours at doses indicated in the figure. Cephalothin is a cephalosporin β-lactam antibiotic to which MRSA is resistant, as shown in the solid black curve. Administration of compound F12 at 20 mg/kg increased the survival from 12 to 42 h (broken line). Combination of F12 (20 mg/kg) with cephalothin (30 mg/kg) further increased survival to 84 h (solid broken line).

This result indicates a synergism between F12 and an antibiotic, indicating resensitization of MRSA to the antibiotic in the presence of the antivirulence compound. Control with F12 in the absence of bacteria resulted in 80% survival after 84 h. Similar results were obtained with compounds F1 and F19.

All publications and patents mentioned herein are incorporated herein by reference to disclose and describe the specific methods and/or materials in connection with which the publications and patents are cited. The publications and patents discussed herein are provided solely for their disclosure prior to the filing date of the present application. Nothing herein is to be construed as an admission that the present invention is not entitled to antedate such publication or patent by virtue of prior invention. Further, the dates of publication or issuance provided may be different from the actual dates, which may need to be independently confirmed.

Having described the invention, the following is claimed:

1. A method of reducing the virulence of bacteria that express AgrA comprising:
administering to the bacteria an amount of an AgrA antagonist effective to inhibit the synthesis of one or more virulence factors by the bacteria, wherein the AgrA antagonist includes the general formula:

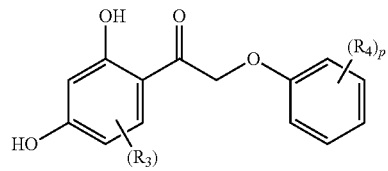

wherein $R_3$ is selected from the group consisting of substituted or unsubstituted 5 $C_3$-$C_6$ alkyl; $R_4$ is selected from the group consisting of halo, nitro, substituted or unsubstituted $C_1$-$C_6$ alkyl, $C_3$-$C_{20}$ aryl, COOH, OCH$_3$, and COOCH$_3$, p is an integer from 0-5; and pharmaceutically acceptable salts thereof.

2. The method of claim 1, wherein $R_3$ is selected from the group consisting of 5-Pr, and 5-Hexyl; $R_4$ is selected from the group consisting of F, Cl, Br, I, NO$_2$, Me, i-Pr, Ph, COOH, t-Bu, OCH$_3$, and COOCH$_3$; wherein p is an integer from 0- 5; and pharmaceutically acceptable salts thereof.

3. The method of claim 1, wherein in the AgrA antagonist is provided in a topical composition with a pharmaceutically acceptable carrier and topically administered to a bacteria infection of a subject.

4. The method of claim 1, further comprising administering an antibiotic to the bacteria.

5. The method of claim 1, wherein the AgrA antagonist includes a compound (4f):

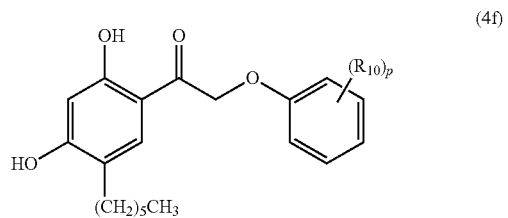

wherein $R_{10}$ is selected from F, Cl, Br, I, NO$_2$, Me, i-Pr, Ph, COOH, t-Bu, OCH$_3$, and COOCH$_3$; p is an integer from 0-5, and pharmaceutically acceptable salts thereof.

6. The method of claim 1, wherein the AgrA antagonist includes a compound having a formula selected from the group consisting of:

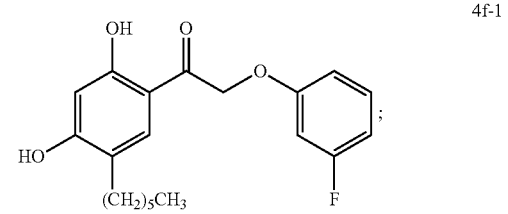

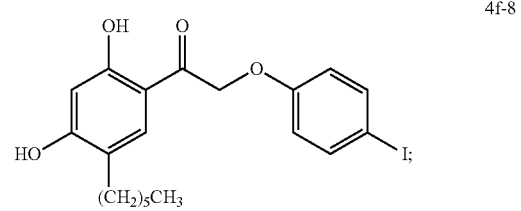

-continued
4f-12 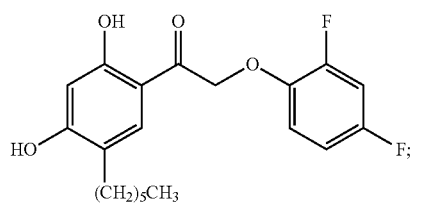
4f-14 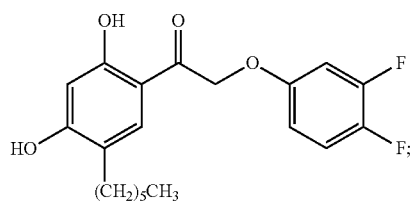
4f-19 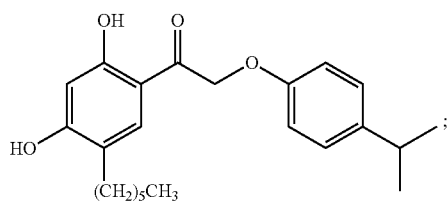
4f-20 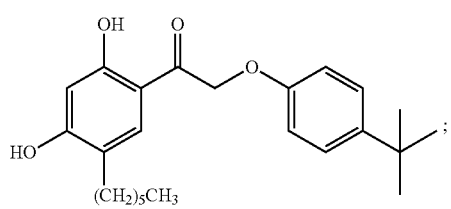
4f-21 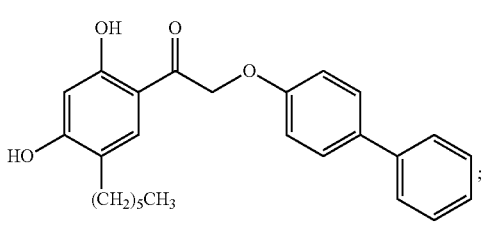
4f-22 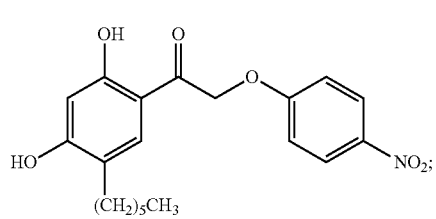
4f-26 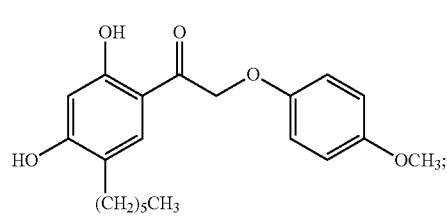
-continued
4f-27 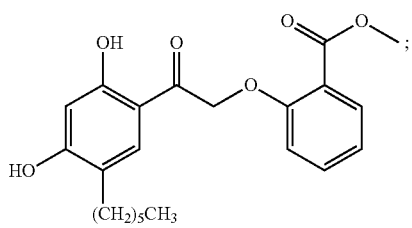
4f-28 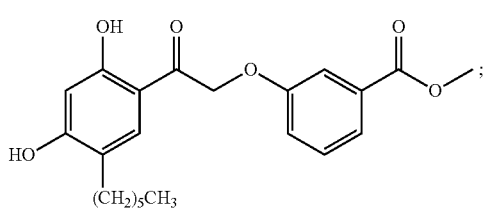
4f-29 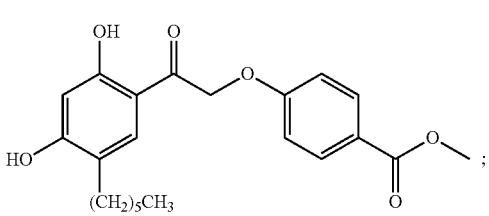
4f-0 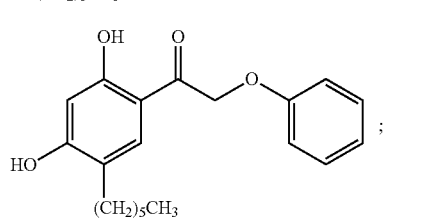
and pharmaceutically acceptable salts thereof.
7. The method of claim 1, wherein the AgrA antagonist includes a compound having a formula selected from the group consisting of:
4f-12 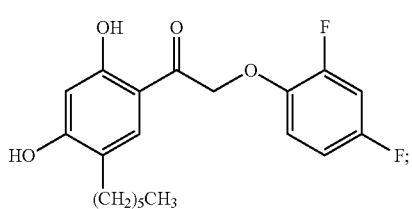
4f-19 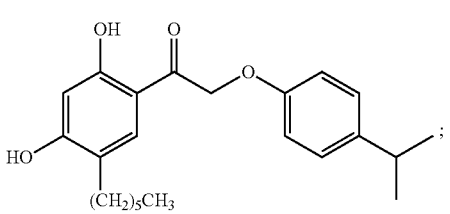
and pharmaceutically acceptable salts thereof.
* * * * *